(12) United States Patent
Müller et al.

(10) Patent No.: US 9,506,943 B2
(45) Date of Patent: Nov. 29, 2016

(54) ALIQUOTTER SYSTEM AND WORKFLOW

(71) Applicant: Beckman Coulter, Inc., Brea, CA (US)

(72) Inventors: Martin Müller, Schliersee-Neuhaus (DE); Charles W. Johns, Brownsburg, IN (US); Michael Eberhardt, Munich (DE)

(73) Assignee: Beckman Coulter, Inc., Brea, CA (US)

( * ) Notice: Subject to any disclaimer, the term of this patent is extended or adjusted under 35 U.S.C. 154(b) by 658 days.

(21) Appl. No.: 13/671,405

(22) Filed: Nov. 7, 2012

(65) Prior Publication Data
US 2013/0125675 A1  May 23, 2013

Related U.S. Application Data

(60) Provisional application No. 61/556,667, filed on Nov. 7, 2011, provisional application No. 61/616,994, filed on Mar. 28, 2012, provisional application No. 61/680,066, filed on Aug. 6, 2012.

(51) Int. Cl.
*G01N 35/10* (2006.01)
*B65G 47/28* (2006.01)
(Continued)

(52) U.S. Cl.
CPC ......... *G01N 35/1009* (2013.01); *B01D 21/262* (2013.01); *B04B 7/02* (2013.01); *B04B 7/08* (2013.01); *B04B 9/146* (2013.01); *B04B 13/00* (2013.01); *B04B 15/00* (2013.01); *B25J 11/00* (2013.01); *B65D 51/24* (2013.01); *B65G 47/28* (2013.01); *G01B 11/02* (2013.01); *G01B 11/08* (2013.01); *G01B 11/10* (2013.01); *G01L 19/08* (2013.01); *G01M 1/14* (2013.01); *G01N 21/27* (2013.01); *G01N 35/0099* (2013.01);
(Continued)

(58) Field of Classification Search
None
See application file for complete search history.

(56) References Cited

U.S. PATENT DOCUMENTS 3,158,765 A  11/1964  Prolgreen
4,052,161 A  10/1977  Atwood et al.
(Continued)

FOREIGN PATENT DOCUMENTS

CA  1 282 692 A1  4/1991
CN  1127887 A  7/1996
(Continued)

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA. Sep. 1999.
(Continued)

*Primary Examiner* — Jill Warden
*Assistant Examiner* — Benjamin Whatley
(74) *Attorney, Agent, or Firm* — Kilpatrick Townsend & Stockton LLP

(57) ABSTRACT

A system is disclosed. The system includes an aliquotter module. The aliquotter module includes a track including: a travel lane; a first loop; and a second loop configured to transport sample carriers with primary sample containers. The aliquotter module can further include a pipettor that can aspirate a first aliquot volume of a sample in a primary sample container located in an aspiration position and dispense the first aliquot volume of the sample in a secondary sample container located in a dispensing position. The aliquotter module can cause the secondary sample container to leave the aliquotter module before the primary sample container.

6 Claims, 13 Drawing Sheets

(51) Int. Cl.

| | | |
|---|---|---|
| *B01D 21/26* | (2006.01) | |
| *B04B 7/08* | (2006.01) | |
| *B04B 15/00* | (2006.01) | |
| *B25J 11/00* | (2006.01) | |
| *B04B 9/14* | (2006.01) | |
| *G01N 35/00* | (2006.01) | |
| *G01N 35/04* | (2006.01) | |
| *G01B 11/02* | (2006.01) | |
| *G01B 11/08* | (2006.01) | |
| *G01B 11/10* | (2006.01) | |
| *G01M 1/14* | (2006.01) | |
| *G01N 21/27* | (2006.01) | |
| *B04B 7/02* | (2006.01) | |
| *B04B 13/00* | (2006.01) | |
| *B65D 51/24* | (2006.01) | |
| *G01L 19/08* | (2006.01) | |
| *B04B 11/04* | (2006.01) | |
| *B01L 3/00* | (2006.01) | |

(52) U.S. Cl.
CPC ........ *G01N35/00732* (2013.01); *G01N 35/04* (2013.01); *G01N 35/10* (2013.01); *B01L 3/5021* (2013.01); *B04B 2011/046* (2013.01); *B04B 2013/006* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *Y10T 29/49826* (2015.01)

(56) References Cited

U.S. PATENT DOCUMENTS

| | | | |
|---|---|---|---|
| 4,101,070 A | 7/1978 | Hoare et al. | |
| 4,119,381 A | 10/1978 | Muka et al. | |
| 4,250,266 A | 2/1981 | Wade | |
| 4,401,189 A | 8/1983 | Majewski | |
| 4,486,539 A | 12/1984 | Ranki et al. | |
| 4,501,495 A | 2/1985 | Faulkner et al. | |
| 4,530,056 A | 7/1985 | MacKinnon et al. | |
| 4,593,238 A | 6/1986 | Yamamoto | |
| 4,593,239 A | 6/1986 | Yamamoto | |
| 4,673,657 A | 6/1987 | Christian | |
| 4,674,640 A | 6/1987 | Asa et al. | |
| 4,676,952 A | 6/1987 | Edelmann et al. | |
| 4,683,195 A | 7/1987 | Mullis et al. | |
| 4,683,202 A | 7/1987 | Mullis | |
| 4,751,177 A | 6/1988 | Stabinsky | |
| 4,780,817 A | 10/1988 | Lofgren | |
| 4,798,095 A * | 1/1989 | Itoh ........................ 73/863.01 |
| 4,800,159 A | 1/1989 | Mullis et al. | |
| 4,851,330 A | 7/1989 | Kohne | |
| 4,865,986 A | 9/1989 | Coy et al. | |
| 4,943,415 A | 7/1990 | Przybylowicz et al. | |
| 4,947,094 A | 8/1990 | Dyer et al. | |
| 4,950,613 A | 8/1990 | Arnold, Jr. et al. | |
| 5,055,393 A | 10/1991 | Kwoh et al. | |
| 5,055,408 A | 10/1991 | Higo et al. | |
| 5,075,853 A | 12/1991 | Luke, Jr. | |
| 5,118,191 A | 6/1992 | Hopkins | |
| 5,147,529 A | 9/1992 | Lee et al. | |
| 5,154,888 A | 10/1992 | Zander et al. | |
| 5,158,895 A | 10/1992 | Ashihara et al. | |
| 5,168,766 A | 12/1992 | Stoffel | |
| 5,179,329 A | 1/1993 | Nishikawa et al. | |
| 5,185,439 A | 2/1993 | Arnold, Jr. et al. | |
| 5,186,827 A | 2/1993 | Liberti et al. | |
| 5,190,136 A | 3/1993 | Greckseh et al. | |
| 5,196,168 A | 3/1993 | Muszak et al. | |
| 5,205,393 A | 4/1993 | Malow et al. | |
| 5,229,297 A | 7/1993 | Schnipelsky et al. | |
| 5,234,665 A | 8/1993 | Ohta et al. | |
| 5,244,055 A | 9/1993 | Shimizu | |
| 5,283,174 A | 2/1994 | Arnold, Jr. et al. | |
| 5,283,739 A | 2/1994 | Summerville et al. | |
| 5,288,463 A | 2/1994 | Chemelli | |
| 5,330,916 A | 7/1994 | Williams et al. | |
| 5,350,564 A | 9/1994 | Mazza et al. | |
| 5,351,801 A | 10/1994 | Markin et al. | |
| 5,362,291 A | 11/1994 | Williamson, IV | |
| 5,366,896 A | 11/1994 | Ooura et al. | |
| 5,374,395 A | 12/1994 | Robinson et al. | |
| 5,375,898 A | 12/1994 | Ohmori et al. | |
| 5,380,487 A | 1/1995 | Choperena et al. | |
| 5,388,682 A | 2/1995 | Dudley | |
| 5,389,339 A | 2/1995 | Petschek et al. | |
| 5,397,709 A | 3/1995 | Berndt | |
| 5,399,491 A | 3/1995 | Kacian et al. | |
| 5,403,711 A | 4/1995 | Walder et al. | |
| 5,415,839 A | 5/1995 | Zaun et al. | |
| 5,422,271 A | 6/1995 | Chen et al. | |
| 5,427,930 A | 6/1995 | Birkenmeyer et al. | |
| 5,437,990 A | 8/1995 | Burg et al. | |
| 5,443,791 A | 8/1995 | Cathcart et al. | |
| 5,445,037 A * | 8/1995 | Itoh ........................ 73/864.25 |
| 5,447,687 A | 9/1995 | Lewis et al. | |
| 5,449,602 A | 9/1995 | Royer et al. | |
| 5,462,881 A | 10/1995 | Perlman | |
| 5,466,574 A | 11/1995 | Liberti et al. | |
| 5,480,784 A | 1/1996 | Kacian et al. | |
| 5,482,834 A | 1/1996 | Gillespie | |
| 5,504,345 A | 4/1996 | Bartunek et al. | |
| 5,514,550 A | 5/1996 | Findlay et al. | |
| 5,525,300 A | 6/1996 | Danssaert et al. | |
| 5,527,673 A | 6/1996 | Reinhartz et al. | |
| 5,536,649 A | 7/1996 | Fraiser et al. | |
| 5,538,849 A | 7/1996 | Uematsu et al. | |
| 5,554,516 A | 9/1996 | Kacian et al. | |
| 5,563,037 A | 10/1996 | Sutherland et al. | |
| 5,578,270 A | 11/1996 | Reichler et al. | |
| 5,582,796 A | 12/1996 | Carey et al. | |
| 5,585,242 A | 12/1996 | Bourma et al. | |
| 5,585,481 A | 12/1996 | Arnold, Jr. et al. | |
| 5,587,128 A | 12/1996 | Wilding et al. | |
| 5,589,333 A | 12/1996 | Bagasra et al. | |
| 5,602,042 A | 2/1997 | Farber | |
| 5,604,130 A | 2/1997 | Warner et al. | |
| 5,612,200 A | 3/1997 | Dattagupta et al. | |
| 5,612,525 A | 3/1997 | Apter et al. | |
| 5,623,415 A | 4/1997 | O'Bryan et al. | |
| 5,628,962 A | 5/1997 | Kanbara et al. | |
| 5,637,275 A | 6/1997 | Carey et al. | |
| 5,639,599 A | 6/1997 | Ryder et al. | |
| 5,639,604 A | 6/1997 | Arnold et al. | |
| 5,641,658 A | 6/1997 | Adams et al. | |
| 5,652,489 A | 7/1997 | Kawakami | |
| 5,653,940 A | 8/1997 | Carey et al. | |
| 5,656,493 A | 8/1997 | Mullis et al. | |
| 5,665,554 A | 9/1997 | Reeve et al. | |
| 5,679,553 A | 10/1997 | Van Gemen et al. | |
| 5,686,272 A | 11/1997 | Marshall et al. | |
| 5,702,950 A | 12/1997 | Tajima | |
| 5,705,062 A | 1/1998 | Knobel | |
| 5,714,380 A | 2/1998 | Neri et al. | |
| 5,720,923 A | 2/1998 | Haff et al. | |
| 5,723,591 A | 3/1998 | Livak et al. | |
| 5,730,938 A | 3/1998 | Carbonari et al. | |
| 5,735,587 A | 4/1998 | Malin et al. | |
| 5,741,708 A | 4/1998 | Carey et al. | |
| 5,746,978 A | 5/1998 | Bienhaus et al. | |
| 5,750,338 A | 5/1998 | Collins et al. | |
| 5,773,268 A | 6/1998 | Korenberg et al. | |
| 5,779,981 A | 7/1998 | Danssaert et al. | |
| 5,786,182 A | 7/1998 | Catanzariti et al. | |
| 5,795,547 A | 8/1998 | Moser et al. | |
| 5,798,263 A | 8/1998 | Wood et al. | |
| 5,814,008 A | 9/1998 | Chen et al. | |
| 5,814,276 A | 9/1998 | Riggs | |
| 5,814,961 A | 9/1998 | Imahashi | |
| 5,827,653 A | 10/1998 | Sammes et al. | |
| 5,846,489 A | 12/1998 | Bienhaus et al. | |

(56) References Cited

U.S. PATENT DOCUMENTS

| | | |
|---|---|---|
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |
| 5,882,903 A | 3/1999 | Andrevski et al. |
| 5,895,631 A | 4/1999 | Tajima |
| 5,897,090 A | 4/1999 | Smith et al. |
| 5,897,783 A | 4/1999 | Howe et al. |
| 5,914,230 A | 6/1999 | Liu et al. |
| 5,919,622 A | 7/1999 | Macho et al. |
| 5,922,591 A | 7/1999 | Anderson et al. |
| 5,925,517 A | 7/1999 | Tyagi et al. |
| 5,928,907 A | 7/1999 | Woudenberg et al. |
| 5,948,673 A | 9/1999 | Cottingham |
| 5,966,309 A | 10/1999 | O'Bryan et al. |
| 5,994,056 A | 11/1999 | Higuchi |
| 6,011,508 A | 1/2000 | Perreault et al. |
| 6,033,574 A | 3/2000 | Siddiqi |
| 6,033,880 A | 3/2000 | Haff et al. |
| 6,043,880 A | 3/2000 | Andrews et al. |
| 6,049,745 A | 4/2000 | Douglas et al. |
| 6,056,106 A | 5/2000 | van Dyke, Jr. et al. |
| 6,060,022 A | 5/2000 | Pang et al. |
| 6,063,340 A | 5/2000 | Lewis et al. |
| 6,068,978 A | 5/2000 | Zaun et al. |
| 6,071,395 A | 6/2000 | Lange |
| 6,100,079 A | 8/2000 | Tajima |
| 6,110,676 A | 8/2000 | Coull et al. |
| 6,110,678 A | 8/2000 | Weisburg et al. |
| 6,117,398 A | 9/2000 | Bienhaus et al. |
| 6,129,428 A | 10/2000 | Helwig et al. |
| 6,150,097 A | 11/2000 | Tyagi et al. |
| 6,165,778 A | 12/2000 | Kedar |
| 6,171,780 B1 | 1/2001 | Pham et al. |
| 6,212,448 B1 | 4/2001 | Xydis |
| 6,277,332 B1 | 8/2001 | Sucholeiki |
| 6,290,907 B1 * | 9/2001 | Takahashi et al. ............. 422/65 |
| 6,300,068 B1 | 10/2001 | Burg et al. |
| 6,300,138 B1 | 10/2001 | Gleason et al. |
| 6,306,658 B1 | 10/2001 | Turner et al. |
| 6,333,008 B1 | 12/2001 | Leistner et al. |
| 6,335,166 B1 | 1/2002 | Ammann et al. |
| 6,353,774 B1 | 3/2002 | Goldenberg et al. |
| 6,368,872 B1 | 4/2002 | Juranas |
| 6,370,452 B1 | 4/2002 | Pfister |
| 6,374,989 B1 | 4/2002 | van Dyke, Jr. et al. |
| 6,377,888 B1 | 4/2002 | Olch |
| 6,429,016 B1 | 8/2002 | McNeil |
| 6,436,349 B1 | 8/2002 | Carey et al. |
| 6,444,171 B1 | 9/2002 | Sakazume et al. |
| RE37,891 E | 10/2002 | Collins et al. |
| 6,458,324 B1 | 10/2002 | Schinzel |
| 6,520,313 B1 | 2/2003 | Kaarakainen et al. |
| 6,548,026 B1 | 4/2003 | Dales et al. |
| 6,586,234 B1 | 7/2003 | Burg et al. |
| 6,586,255 B1 | 7/2003 | Hubert et al. |
| 6,597,450 B1 | 7/2003 | Andrews et al. |
| 6,599,476 B1 | 7/2003 | Watson et al. |
| 6,605,213 B1 | 8/2003 | Ammann et al. |
| 6,629,028 B2 | 9/2003 | Paromtchik et al. |
| 6,633,785 B1 | 10/2003 | Kasahara et al. |
| 6,692,708 B2 | 2/2004 | Chandler, Jr. |
| 6,764,649 B2 | 7/2004 | Ammann |
| 6,770,883 B2 | 8/2004 | Mc Neal et al. |
| 6,818,183 B2 | 11/2004 | Hajduk et al. |
| 6,890,742 B2 | 5/2005 | Ammann et al. |
| 6,919,058 B2 | 7/2005 | Andersson et al. |
| 6,919,175 B1 | 7/2005 | Bienhaus et al. |
| 6,941,200 B2 | 9/2005 | Sonoyama et al. |
| 6,993,176 B2 | 1/2006 | Yamagishi et al. |
| 6,999,847 B2 | 2/2006 | Barry et al. |
| 7,028,831 B2 | 4/2006 | Veiner |
| 7,033,820 B2 | 4/2006 | Ammann et al. |
| 7,045,358 B2 | 5/2006 | Chandler, Jr. |
| 7,071,006 B2 | 7/2006 | Tajima et al. |
| 7,078,698 B2 | 7/2006 | Itoh |
| 7,118,892 B2 | 10/2006 | Ammann et al. |
| 7,135,145 B2 | 11/2006 | Ammann et al. |
| 7,174,836 B2 | 2/2007 | Marino et al. |
| 7,237,749 B2 | 7/2007 | Ritts et al. |
| 7,264,111 B2 | 9/2007 | Veiner |
| 7,267,795 B2 | 9/2007 | Ammann et al. |
| 7,269,480 B2 | 9/2007 | Hashimoto et al. |
| 7,288,229 B2 | 10/2007 | Turner et al. |
| 7,362,258 B2 | 4/2008 | Kawabe et al. |
| 7,419,830 B2 | 9/2008 | Canos et al. |
| 7,463,948 B2 | 12/2008 | Orita |
| 7,473,897 B2 | 1/2009 | Braendle et al. |
| 7,482,143 B2 | 1/2009 | Ammann et al. |
| 7,499,581 B2 | 3/2009 | Tribble et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,688,448 B2 | 3/2010 | Bamberg et al. |
| 7,771,659 B2 | 8/2010 | Ziegler |
| 8,074,578 B2 | 12/2011 | Thornton |
| 8,192,992 B2 | 6/2012 | Ammann et al. |
| 2002/0025064 A1 | 2/2002 | Itoh |
| 2002/0028489 A1 | 3/2002 | Ammann et al. |
| 2002/0031768 A1 | 3/2002 | McMillan et al. |
| 2002/0062111 A1 * | 5/2002 | Itoh ............................ 604/318 |
| 2002/0077239 A1 | 6/2002 | Evans, III et al. |
| 2002/0086417 A1 | 7/2002 | Chen |
| 2002/0098117 A1 | 7/2002 | Ammann et al. |
| 2002/0123156 A1 | 9/2002 | Tajima |
| 2002/0137194 A1 | 9/2002 | Ammann et al. |
| 2002/0137197 A1 | 9/2002 | Ammann et al. |
| 2002/0146347 A1 | 10/2002 | McNeil |
| 2002/0147515 A1 | 10/2002 | Fava et al. |
| 2003/0026736 A1 | 2/2003 | Hajduk et al. |
| 2003/0027206 A1 | 2/2003 | Ammann et al. |
| 2003/0054542 A1 | 3/2003 | Burns et al. |
| 2003/0129614 A1 | 7/2003 | Parameswaran et al. |
| 2003/0190755 A1 | 10/2003 | Turner et al. |
| 2003/0213313 A1 | 11/2003 | Katagi |
| 2003/0223916 A1 | 12/2003 | Testrut et al. |
| 2004/0029260 A1 | 2/2004 | Hansen et al. |
| 2004/0076983 A1 | 4/2004 | Karlsen |
| 2004/0087426 A1 | 5/2004 | Lattanzi |
| 2004/0115796 A1 | 6/2004 | Burns |
| 2004/0158355 A1 | 8/2004 | Holmqvist et al. |
| 2004/0184959 A1 | 9/2004 | Itoh |
| 2004/0206419 A1 | 10/2004 | Ganz et al. |
| 2004/0213651 A1 | 10/2004 | Malin |
| 2005/0036907 A1 * | 2/2005 | Shoji ............................ 422/58 |
| 2005/0130198 A1 | 6/2005 | Ammann et al. |
| 2005/0158212 A1 | 7/2005 | Yavilevich |
| 2005/0163354 A1 | 7/2005 | Ziegler |
| 2005/0207937 A1 | 9/2005 | Itoh |
| 2005/0220670 A1 | 10/2005 | Palmieri et al. |
| 2005/0233370 A1 | 10/2005 | Ammann et al. |
| 2005/0239127 A1 | 10/2005 | Ammann et al. |
| 2005/0266489 A1 | 12/2005 | Ammann et al. |
| 2005/0271555 A1 | 12/2005 | Itoh |
| 2006/0003373 A1 | 1/2006 | Ammann et al. |
| 2006/0014295 A1 | 1/2006 | Ziegler |
| 2006/0020370 A1 | 1/2006 | Abramson |
| 2006/0148063 A1 | 7/2006 | Fauzzi et al. |
| 2006/0228268 A1 | 10/2006 | Heimberg et al. |
| 2007/0044676 A1 | 3/2007 | Clark et al. |
| 2007/0059209 A1 | 3/2007 | Pang et al. |
| 2007/0100498 A1 | 5/2007 | Matsumoto et al. |
| 2007/0110634 A1 | 5/2007 | Heimberg et al. |
| 2007/0134131 A1 | 6/2007 | Watson et al. |
| 2007/0179690 A1 | 8/2007 | Stewart |
| 2007/0184548 A1 | 8/2007 | Tan et al. |
| 2007/0193859 A1 * | 8/2007 | Kyutoku et al. ............. 198/787 |
| 2007/0196237 A1 | 8/2007 | Neuzil et al. |
| 2007/0208440 A1 | 9/2007 | Bliss et al. |
| 2007/0225901 A1 | 9/2007 | Yamaguchi |
| 2007/0225906 A1 | 9/2007 | Ikeda |
| 2008/0014181 A1 | 1/2008 | Ariff et al. |
| 2008/0015470 A1 | 1/2008 | Sarstedt |

(56) References Cited

U.S. PATENT DOCUMENTS

| | | | |
|---|---|---|---|
| 2008/0056958 A1 | 3/2008 | Vijay et al. | |
| 2008/0069730 A1* | 3/2008 | Itoh | 422/65 |
| 2008/0138249 A1* | 6/2008 | Itoh | 422/100 |
| 2008/0167817 A1 | 7/2008 | Hessler et al. | |
| 2008/0241837 A1 | 10/2008 | Ammann et al. | |
| 2008/0255683 A1 | 10/2008 | Takahashi et al. | |
| 2008/0268528 A1 | 10/2008 | Ammann et al. | |
| 2008/0274511 A1 | 11/2008 | Tan et al. | |
| 2008/0297769 A1 | 12/2008 | Bamberg et al. | |
| 2009/0029352 A1 | 1/2009 | Ammann et al. | |
| 2009/0029871 A1 | 1/2009 | Ammann et al. | |
| 2009/0029877 A1 | 1/2009 | Ammann et al. | |
| 2009/0030551 A1 | 1/2009 | Hein et al. | |
| 2009/0035185 A1 | 2/2009 | Tsujimura et al. | |
| 2009/0042281 A1 | 2/2009 | Chang et al. | |
| 2009/0047179 A1 | 2/2009 | Ping et al. | |
| 2009/0117620 A1 | 5/2009 | Fritchie et al. | |
| 2009/0318276 A1 | 12/2009 | Miller | |
| 2009/0324032 A1 | 12/2009 | Chen | |
| 2010/0018330 A1 | 1/2010 | Marty et al. | |
| 2010/0115887 A1 | 5/2010 | Schroeder et al. | |
| 2010/0129789 A1 | 5/2010 | Self et al. | |
| 2010/0141756 A1 | 6/2010 | Grote et al. | |
| 2010/0261595 A1 | 10/2010 | Schaefer et al. | |
| 2010/0291619 A1* | 11/2010 | Robinson et al. | 435/34 |
| 2011/0065193 A1 | 3/2011 | Kitagawa et al. | |
| 2011/0226584 A1* | 9/2011 | Ek | 198/340 |
| 2012/0058010 A1* | 3/2012 | Pedrazzini | 422/63 |
| 2012/0129673 A1 | 5/2012 | Fukugaki et al. | |
| 2012/0266698 A1* | 10/2012 | Isobe et al. | 73/863.92 |
| 2013/0123089 A1 | 5/2013 | Johns et al. | |
| 2013/0126302 A1 | 5/2013 | Johns et al. | |
| 2013/0128035 A1 | 5/2013 | Johns et al. | |
| 2013/0129166 A1 | 5/2013 | Mueller et al. | |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| CN | 101149386 A | 3/2008 |
| CN | 101251546 A | 8/2008 |
| DE | 35 10 797 C2 | 1/1988 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 794 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 01-211500 A1 | 8/1989 |
| JP | 1-287464 A | 11/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-062426 A | 3/1998 |
| JP | 11-500224 A | 1/1999 |
| JP | 11-503315 A | 3/1999 |
| JP | 11-264828 A | 9/1999 |
| JP | 11-304814 A | 11/1999 |
| JP | 2000-500331 A | 1/2000 |
| JP | 3007571 B2 | 2/2000 |
| JP | 2000-266760 A | 9/2000 |
| JP | 2001-503730 A | 3/2001 |
| JP | 2002-296286 A | 10/2002 |
| JP | 2005-300220 A | 10/2005 |
| JP | 2008-076185 A | 9/2006 |
| JP | 2006-317330 A | 11/2006 |
| JP | 2007-249632 A | 9/2007 |
| JP | 2008-032652 A2 | 2/2008 |
| JP | 2008-145194 A | 6/2008 |
| JP | 4511034 B2 | 5/2010 |
| JP | 2010-526289 A | 7/2010 |
| JP | 4662580 B2 | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |

(56) References Cited

FOREIGN PATENT DOCUMENTS

| | | |
|---|---|---|
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/25712 A1 | 8/1996 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2008/133708 A1 | 11/2008 |
| WO | 2009/068555 A1 | 6/2009 |
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2010/105992 A1 | 9/2010 |
| WO | WO 2010105992 A1 * | 9/2010 |
| WO | 2011/013701 A1 | 2/2011 |
| WO | 2011/028166 A1 | 3/2011 |
| WO | 2011/040196 A1 | 4/2011 |
| WO | WO 2011040196 A1 * | 4/2011 |
| WO | 2012/090795 A1 | 7/2012 |
| WO | 2012/158541 A1 | 11/2012 |

OTHER PUBLICATIONS

ABI Prism® 373 DNA Sequencer With XL Upgrade—User's Manual, Mar. 2001, TOC-iii-TOC-v & 6-11-6-16, Applied Biosystems, USA.

Abravaya, "Strategies to Avoid Amplicon Contamination," in Nucleic Acid Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA. vol. 39, No. 2, Mar. 1994, pp. 362-372.

Akduman et al., "Evaluation of a Strand Displacement Amplification Assay (BD ProbeTec-SDA) for Detection of Neisseria gonorrhoeae in Urine Specimens," J. Clin. Microbiol., 2002, 40(1):281-282, American Society for Microbiology, Washington D.C., USA. Jan. 2002, pp. 281-283.

Amplification Technical Bulletin, "Comparison of TMA with PCR and LCR Amplification Methods," undated, Gen-Probe Incorporated, San Diego, USA, 1 page. by Apr. 1, 2014.

Analog Device; "±5 g to ±5 g, Low Noise, Low Power, Single/Dual Axis / MEMS® Accelerometers,"; http://hibp.ecse.rpi.edu/~connor.education/EISpecs/ADXL150_250_0.pdf;; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Armstrong et al., 1996, "Automated high throughput RT-PCR," Laboratory Robotics and Automation 8:311-315, VCH Publishers, USA.

Astle, "Standards in Robotics and Instrucmentation," Society Updates, Working Group Updates, and Conference Highlights, J. Biomol. Screen., 1996, 1(4):161-172, Sage Publications, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia, vol. 6, No. 5, Oct. 1996.

Belgrader et al., "Automated DNA Purification and Amplification from Blood-Stained Cards Using a Robotic Workstation," Short Technical Reports, Biotechniques, 1995 19(9): Informa Healthcare USA, Inc., UK, pp. 426-428, 430, 432.

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.

Boyd et al., "Robotics and the changing face of the clinical laboratory," Clin. Chem., 1996, 42(12):1901-1910, Washington DC American Association for Clinical Chemistry, USA.

Brochure, "Amplified Mycobacteria Direct Tests," undated, Gen-Probe Incorporated, San Diego, USA, 6 pages, by Apr. 1, 2014.

Brochure, "Introducing the Amplified *Mycobacterium tuberculosis* Direct (MTD) Test from Gen-Probe," Oct. 1996, Gen-Probe Incorporated, San Diego, USA, 2 pages.

Brochure, "The Future of Amplification Technology has Arrived," Oct. 1995, Gen-Probe Incorporated, San Diego, USA, 4 pages.

Buhlmann et al., "An Open Software Environment to Optimize the Productivity of Robotized Laboratories," J. Chromatogra. Sci., 1994, 32:243-248, Preston Technical Abstracts, Niles, USA, Jun. 1994.

Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA. Feb. 1992.

Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.

Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28, 1998; pp. 1-5.

Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA, cover+abstract page.

Carrino et al., "Nucleic Acid Amplification Methods," J. Micorbiol. Methods, 1995, 23:3-20.

(56) References Cited

OTHER PUBLICATIONS

Check, "Real-time PCR for the rest of us," CAP Today, Jun. 2006, College of American Pathologists, Skokie, IL, USA, 6 pages.
Chemistry Guide, "Automated DNA Sequencing," PE Applied Biosystems, 1998, pp. 1-4~1-6, The Perkin-Elmer Corporation.
Cimino et al., "Post-PCR sterilization: a method to control carry-over contamination for the polymerase chain reaction," Nucleic Acids Res., 1991, 19(1):99-107, Oxford University Press, Oxford, United Kingdom.
Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.
Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.
Corrected Request for *Inter Partes* Reexamination of U.S. Pat. No. 7,482,143, filed on Sep. 14, 2012, 121 pages.
Crotchfelt et al., "Detection of Chlamydia trachomatis by the Gen-Probe Amplified Chlamydia Trachomatis Assay (AMP CT) in Urine Specimens from Men and Women and Endocervical Specimens from Women," J. Clin. Microbiol., Feb. 1998, 36(2):391-394, American Society for Microbiology, Washington D.C., USA.
Davis et al., "Amplification of DNA Using the Polymerase Chain Reaction," in Basic Methods in Molecular Biology, 2nd ed., 1994, p. 121, Appleton & Lange, Norwalk, USA.
Diamandis, "Automation of molecular diagnostics," Clinical Chemistry, 1996, 42:7-8, American Association for Clinical Chemistry, USA.
DiDomenico et al., "COBAS AMPLICOR™: fully automated RNA and DNA amplification and detection system for routine diagnostic PCR," Clin. Chem., 1996, 42(12):1915-1923, Washington DC American Association for Clinical Chemistry, USA.
Dieffenbach et al., "Setting Up a PCR Laboratory," Genome Rsearch, PCR Methods and Applications, 1993, 3:s2-s7, Cold Spring Harbor Laboratory, Cold Spring Harbor, USA.
Dragon, "Handling Reagents in the PCR Laboratory," Genome Research, PCR Methods and Applications, 1993, 3:s8-s9, Cold Spring Harbor Laboratory, Cold Spring Harbor, USA.
Dynal®, Technical Handbook. Molecular Biology, First Edition. "Dynabeads® biomagnetic separation system," 1992, 4 pages, Dynal AS, Norway.
Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.
Espy et al., "Dependence of polymerase chain reaction product inactivation protocols on amplicon length and sequence composition," J. Clin. Microbiol., 1993, 31(9):2361-2365, American Society for Microbiology, Washington D.C., USA, Sep. 1993.
Farrell, Jr., "RT PCR" in RNA Method: A Laboratory Guide for Isolation and Characterization, 1998, 2nd ed., Chapter 15, Academic Press, San Diego, California, USA, pp . 296, 298, 300, 302, 304, 306.
Feinberg, "A Technique for Radiolabeling DNA Restriction Endonuclease Fragments to High Specific Activity", Analytical Biochemistry, 1983, 132:6-13, Academic Press, USA.
Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.
Fiore et al., "The Abbott IMx automated benchtop immunochemistry analyzer system," Clin. Chem., 1988, 34 (9):1726-32, American Association for Clinical Chemistry, Washington D.C., USA.

Flexlink®; "TX45E puck handling (mx. 250g),"; located at http://www.flexlink.com/en/offering/conveyor-systems/pallet-and-puck-handling/x45e.jsp; last visited on Jul. 20, 2013; 2 pages.
Friendenberg et al., "Developing a fully automated instrument for molecular diagnostic assays," IVD Technology, 2005, 11(6), 6 pages, A Canon Communications, Los Angeles, USA, Jul./Aug. 2005.
Furrows et al., "Good laboratory practice' in diagnostic laboratories using nucleic acid amplification methods," Clin. Microbiol. Infect., 2001, 7(5):227-229, Blackwell Science, Oxford, United Kingdom, May 2001.
Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.
Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA, Sep. 1997.
Gibson et al., "A homogenous method for genotyping with fluorescence polarization," Clin. Chem., 1997, 43(8):1336-1341, American Association for Clinical Chemistry, Washington D.C., USA.
Gibson et al., "A novel method for real time quantitative RT-PCR," Genome Methods, 1996, 6:995-1001, Cold Spring Harbor Laboratory Press, Cold Spring Harbor, USA.
Giesendorf et al., "Molecular beacons: a new approach for semiautomated mutation analysis," Clin. Chem., 1998, 44(3):482-486, American Association for Clinical Chemistry, Washington D.C., USA.
Gilgen et al., "Hydroxyquinoline overcomes PCR inhibition by UV-damaged mineral oil," Nucleic Acids Res., 1995, 23(19):4001-4002, Oxford University Press, Oxford, United Kingdom.
Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA, Sep. 2004.
Godfrey-Faussett, "Molecular Diagnosis of Tuberculosis: The Need for New Diagnostic Tools," Thorax, 1995, 50(7):709-711, British Medical Association, London, United Kingdom.
Greenstein, "Preparing and Using M13-Derived Vectors," Current Protocols in Molecular Biology, published 1990, §1.151 and 1.15.4, J. Wiley and Sons, USA.
Haas, "Clinical Instrumentation (General Chemistry and Immunoassay Analyzers)," Anal. Chem., 1993, 65(12):444R-449R, American Chemical Society, Washington D.C., USA, Jun. 1993.
Haglund et al., "Polymerase Chain Reaction," in Forensic Taphonomy: the Postmortem Fate of Human Remains, 1997, p. 114-115, CRC Press LLC, Boca Raton, USA.
Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.
Hawker, "Laboratory Automation: Total and Subtotal," Clin. Lab. Med., 2007, 27:749-770, Elsevier Health Sciences Division, Philadelphia, USA.
Hawkes et al., "Asymptomatic carriage of *Haemophilus ducreyi* confirmed by the polymerase chain reaction," J. Genitourin. Med., 1995, 71:224-227.
Hawkins et al., "A Magnetic Attraction to High-Throughput Genomics," Science, 1997, 276:1887 & 1889 (p. 1888 omitted—advertisement only), Washington, DC: American Association for the Advancement of Science, USA. Jun. 1997.
Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.
Heid et al., "Real Time Quantitative PCR," Genome Research, 1996, 6:986-994, Cold Spring Harbor Laboratory Press, Cold Spring Harbor, USA.
Hellyer et al., "Letter to the Editor: Specificity of IS6110-Based Amplification Assays for Mycobacterium tuberculosis Complex," J.

(56) References Cited

OTHER PUBLICATIONS

Clin. Microbiol., 1997, 35(3):799-801, American Society for Microbiology, Washington D.C., USA. Mar. 1997.
Herring et al., "ELISA Automation: A Biomek 1000 to Biomek 2000 Comparison of Clinical ELISAs", Application Information, 1995, Beckman Industries, Inc., USA, pp. 1-6.
Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.
Hicks et al., "Beckman/Sagian "Core" Molecular Biology System,", T-1845A, Beckman Instruments, Inc., 1997, 4 pages.
Higuchi et al., "Simultaneous Amplification and Detection of Specific DNA Sequences," Bio/Technology, 1992, 10:413-417, Nature Publishing Company, New York, USA, Apr. 1992.
Hildebrandt et al Development of an Automated Sample Preparation Method for HCV, J. Microbiol. Methods, 1997, 30:235-253, Abstract 17, 1 page, Elsevier Biomedical, Amsterdam, Netherlands.
Hill, "Gen-Probe Transcription-Mediated Amplification: System Principles," Jan. 1996, Gen-Probe Incorporated, San Diego, USA, 4 pages.
Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.
Hill, "Molecular diagnostic testing for infectious diseases using TMA technology," Expert Rev. Mol. Diagn., 2001, 1 (4):445-455, Future Drugs Ltd., London, United Kingdom.
Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.
Hill, "Molecular Diagnostics for Infectious Diseases," J. Clin. Ligand Assay, 1996, 19(1):43-52, Clinical Ligand Assay Society, Wayne, Michigan, USA. Spring 1996.
Hoad et al., "Virus Genome Detection by the PCR," in Practical Molecular Virology: Viral Vectors for Gene Expression, 1991, pp. 75-76, Humana Press, Totowa, USA.
Holland et al., "Detection of specific polymerase chain reaction product by utilizing the 5'→ 3' exonuclease activity of Thermus aquaticus DNA polymerase," Biochemistry, 1991, 88:7276-7280, Proc. Natl. Acad. Sci. USA, Washington D.C., USA, Aug. 1991.
International Search Report and Written Opinion mailed on Feb. 15, 2013 for PCT Application No. PCT/US2012/063923, 12 pages.
International Search Report and Written Opinion mailed on Feb. 15, 2013 for PCT Application No. PCT/US2012/063914, 9 pages.
International Search Report and Written Opinion mailed on Jun. 12, 2013 for PCT Patent Application No. PCT/US2012/063888, 18 pages.
International Search Report and Written Opinion mailed on Mar. 19, 2013 for PCT Application No. PCT/US2012/063929, 13 pages.
International Search Report and Written Opinion mailed on Dec. 7, 2012 for PCT Patent Application No. PCT/US2011/045107, 18 pages.
International Search Report and Written Opinion mailed on Oct. 4, 2013 for PCT Patent Application No. PCT/US2012/063931, 24 pages.
International Search Report and Written Opinion mailed on Sep. 30, 2013 for PCT Patent Application No. PCT/US2012/063930, 37 pages.
Invitation to Pay Additional Fees mailed on Mar. 1, 2013 for PCT Patent Application No. PCT/US2012/063918, 6 pages.
Invitation to Pay Additional Fees mailed on Mar. 19, 2013 for PCT Patent Application No. PCT/US2012/063930, 8 pages.
Invitation to Pay Additional Fees mailed on Mar. 25, 2013 for PCT Patent Application No. PCT/US2012/063931, 8 pages.
Invitation to Pay Additional Fees mailed on Mar. 6, 2013 for PCT Patent Application No. PCT/US2012/063888, 6 pages.
Invitrogen; Manual, "Dynabeads® DNA Direct™ Blood" Cat. No. 631.02 "For the isolation of PCR-ready genomic DNA from blood" Rev. o. 006, Invitrogen, *Dynal® Invitrogen Bead Separations*, 2007, pp. 1-20.

Jaklevic, "Automation of High-Throughput PCR Assays," Laboratory Robotics and Automation, 8(5):277-286, John Wiley & Sons Inc., USA.
Jaton et al., "Development of polymerase chain reaction assays for detection of Listeria monocytogenes in clinical cerebrospinal fluid samples," J. Clin. Microbiol., 1992, 30(8):1931-1936, American Society for Microbiology, Washington D.C., USA, Aug. 1992.
Jungkind et al., "Evaluation of Automated COBAS AMPLICOR PCR System for Detection of Several Infectious Agents and Its Impact on Laboratory Management," J. Clin. Microbiol., 1996, 34(11):2778-2783, American Society for Microbiology, Washington, D.C., USA. No39v. 1996.
Kalinina et al., "Nanoliter scale PCR with TaqMan detection," Nucleic Acids Res., 1997, 25(10):1999-2004, Oxford University Press, Oxford, United Kingdom.
Kapperud et al., "Detection of Pathogenic Yersinia enterocolitica in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA, Sep. 1993.
Kendrew et al., "Polymerase Chain Reaction," in The Encyclopedia of Molecular Biology, 1994, pp. 864-865, Blackwell Science Ltd., Cambridge, USA.
Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.
Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.
Kolmodin et al., "Basic Principles and Routine Practice," in PCR Cloning Protocols From Molecular Cloning to Genetic Engineering, 1997, pp. 3-5, Humana Press, Totowa, USA.
Kost, G. J., *Handbook of Clinical Automation, Robotics, and Optimization*; Chapters 1, 10, and 12-14; 1996 by John Wiley & Sons, Inc.; 189 pages total.
Kretz et al., "Cycle sequencing," PCR Methods and Applications, 1994, 3:S107-S112, Cold Spring Harbor Laboratory, Cold Spring Harbor Press, USA.
Krieg, "Quantification of RNA by Competitive RT PCR," in a Laboratory Guide to RNA, 1996, p. 210, Wiliey-Liss, New York City, USA.
Kwok et al., "Avoiding False Positive with PCR," Nature, 1989, 339:237-238, Nature Publishing Group, Basingstoke, USA, May 1989.
Landry, "False-Positive Polymerase Chain Reaction Results in the Diagnosis of Herpes Simplex Encephalitis," J. Infect. Dis., 1995, 172(6): ,University of Chicago Press, Chicago, USA, Dec. 1995, pp. 1641-1643.
Lay et al., "Real-time fluorescence genotyping of factor V Leiden during rapid-cycle PCR," Clin. Chem., 1997, 43(12):2262-2267, American Association for Clinical Chemistry, Washington D.C., USA.
Lee et al., "Direct Identification of *Vibrio vulmificus* in Clinical Specimens by Nested PCR," J. Clin. Microbial., 1998, 36 (10):2887-2892, American Society for Microbiology, Washington D.C., USA, Oct. 1998.
Lee et al., "Nucleic Acid Amplification Technologies: Application to Disease Diagnosis," BioTechniques Books, 1997, Eaton Publishing, Massachusetts, USA, pp. 1-27, 29-91, 197-199, 201-243, 245-255, 257-286.
Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.
Lisby, "Application of Nucleic Acid Amplification in Clinical Microbiology," in Methods in Molecular Biology: PCR in Bioanalysis, 1998, pp. 1-29, Humana Press, Totowa, USA.
Livak et al., "Oligonucleotides with Fluorescent Dyes at Opposite Ends Provide a Quenched Probe System Useful for Detecting PCR Product and Nucleic Acid Hybridization," PCR Methods and Appli-

(56) References Cited

OTHER PUBLICATIONS cations, 1995, 4:357-362, Cold Spring Harbor Laboratory Press, Cold Spring Harbor, New York, USA.

Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.

Lo, "Setting Up a PCR Laboratory," in Methods in Molecular Medicine: Clinical Applications of PCR, 1998, pp. 11-17, Humana Press, Totowa, USA.

Longo, "Use of uracil DNA glycosylase to control carry-over contamination in polymerase chain reactions" Gene, 1990, 93: 125-128, Elsevier/North-Holland, Amsterdam.

Mabilat et al., "Routine Identification of *Mycobacterium tuberculosis* Complex Isolates by Automated Hybridization," J. Clin. Microbiol., 1994, 32(11):2702-2705, American Society for Microbiology, Washington, D.C., USA, Nov . 1994.

Magnemotion; "MagneMover™ LITE,"; located at http://www.magnemotion.com/industrial-automation/magmoverlite.cfm; last visited on Jul. 20, 2013; 3 pages.

Mangiapan, "Sequence capture-PCR improves detection of mycobacterial DNA in clinical specimens" J Clin Microbiol., 1996, 34: 1209-1215, American Society for Microbiology, USA, vol. 34, No. 5, May 1996.

Martin et al., "PCR and Its Modifications for the Detection of Infectious Disease," Nucleic Acid Amplification Technologies: Application to Disease Diagnosis, 1997, Eaton Pub. Co., Massachusetts, USA, pp. 79-99.

McCreedy et al., "Laboratory Design and Work Flow," Diagnostic Molecular Microbiology Principles and Applications, 1993, p. 149-159, Mayo Foundation, Rochester, USA.

Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.

Mercier et al., "Direct PCR from whole blood, without DNA extraction," Nucleic Acids Res., 1990, 18(19):5908, Oxford University Press, Oxford, United Kingdom.

Merel et al., "Completely Automated Extraction of DNA from Whole Blood," Clin. Chem., 1996, 42(8):1285-1286, American Association for Clinical Chemistry, USA.

Merel et al., "Perspectives on Molecular Diagnostics Automation," JALA, 2005, 10:342-350, Association for Laboratory Automation, Charlottesville, USA, Oct. 2005.

Meyers, "PCR Technology," Molecular Biology and Biotechnology: A Comprehensive Desk Reference, 1995, pp. 642-646, VCH Publishers Inc., New York City, USA.

Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.

Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.

Mullis, "Eine Nachtfahrt and die Polymerase-Kettenreaktion," Spektrum der Wissenschaft, 1950, pp. 60-67, Germany.

Muramatsu et al., "Molecular Cell Biology Dictionary," 1997, Tokyo Kagaku Dojin Publisher, Tokyo, Japan, English Translation, 10 pages.

Nace, "Automation in Molecular Diagnostics: A Pleasant Surprise," Advance for Medical Laboratory Professionals, 2006, 14(11):64, Merion Publications, King of Prussia, PA, USA.

Nazarenko et al., "A closed tube format for amplification and detection of DNA based on energy transfer," Nucleic Acids Res., 1997, 25(12):2516-2521, Oxford University Press, Oxford, United Kingdom.

Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.

Newton et al., "Instrumentation, Reagents and Consumables," PCR, 2nd ed., Chpt. 2, pp. 9-28, Bios Scientific, UK, 1997.

Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA, Nov. 1990.

Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.

Noordhoek et al., "Reliability of Nucleic Acid Amplification for Detection of *Mycobacterium tuberculosis*: an International Collaborative Quality Control Study Among 30 Laboratories," J. Clin. Microbiol., 1996, 34(10):2522-2524, American Society for Microbiology, Washington D.C., USA, Oct. 1996.

Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.

Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA, Nov. 1996.

Olive, "Q-Beta Replicase Assays for the Clinical Detection of Infectious Agents,"in Nucleic Acid Amplification Technologies: Application to Disease Diagnosis, 1997, p. 110, Eaton Pub. Co., Natick, USA.

Olsvik et al., "Magnetic Separation Techniques in Diagnostic Microbiology," Clin. Microbiol. Rev., 1994, 7(1):43-54, American Society for Microbiology, Washington, D.C., USA, Jan. 1994.

Oste, "Polymerase Chain Reaction," Product Application FOCUS, BioTechniques, 1988, 6(2):162-167, Informa Healthcare USA, Inc., UK.

Package Insert, "APTIMA® Assay for *Neisseria gonorrhoeae*," IN0148-01-Reg, Rev. 1, Nov. 2004, Gen-Probe Incorporated, San Diego, USA, 20 pages.

Package Insert, "APTIMA® HCV RNA Qualitative Assay," 500237 Rev. B, Jul. 2006, Gen-Probe Incorporated, San Diego, USA, 18 pages.

Patel et al., "Death from Inappropriate Therapy for Lyme Disease," Clin. Infect. Dis., 2000, 31:1107-1109, The University of Chicago Press, Chicago, USA.

Patterson et al., "Random and continuous-access immunoassays with chemiluminescent detection by Access automated analyzer," Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Request for *Inter Partes* Reexamination of U.S. Pat. No. 7,524,652, filed on Sep. 15, 2012, 134 pages.

Riggio et al., "Identification by PCR of Helicobacter pylori in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

(56) References Cited

OTHER PUBLICATIONS

Rudi et al., "Rapid, Universal Method to Isolate PCR-Ready DNA Using Magnetic Beads," BioTechniques, 1997, 22(3):506-511, Informa Healthcare USA, Inc., UK, Mar. 1997.

Rudi, et al., "Detection of Toxin-Producing Cyanobacteria by Use of Paramagnetic Beads for Cell Concentration and DNA Purification," 1998, Appl. Environ Microbiol., 64(1):34-37, Am. Society of Microbiol., USA, Jan. 1998.

Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357, Dec. 1997.

Skeggs, "An automatic method for colorimetric analysis," Am. J. Clin. Pathol., 1957 28:311-322, American Society of Clinical Pathologists, Chicago, USA, vol. 28, No. 3.

Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.

Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA, Jun. 1997.

Smith et al., "Performance of an Automated Q-Beta Replicase Amplification Assay for *Mycobacterium tuberculosis* in a Clinical Trial," J. Clin. Microbiol., 1997, 35(6):1484-1491, Am. Society for Microbiology, USA, Jun. 1997.

Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.

Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.

Stone et al., "Detection of rRNA from four respiratory pathogens using an automated Qβ replicase assay," Mol. Cell. Probes, 1996, 10:359-370, Academic Press Limited, San Diego, California, USA.

Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.

Sutton et al., "Hands Free Polymerase Chain Reaction," International Symposium on Laboratory Automation and Robotics, Oct. 17-20, 1993, p. 326-336, Boston, USA.

Sutton et al., "PCR Has Outgrown Appropriate Automated Instrumentation But Help is on the Way," Today's Chemist at Work, 1995, American Chemical Society, Washington, D.C., USA. pp. 42-43, 45, 47-48.

Taos Inc. "TCS230 Programmable Color to Light-to-Frequency Converter," www.http?pdfl.alldatasheet.com/datasheet-pdf/view/96470/ETC/TCS230.html; Jan. 31, 2003, pp. 1-8.

Techne PHC-3 Thermal Cycler—Techni, Jun. 2009, Pegasus Scientific Inc., USA, 1 page.

Tjian, "Purification and comparative properties of the delta and sigma subunits of RNA polymerase from Bacillus subtilis" Eur. J. Biochem., 1977, 74:149, Blackwell Science Ltd. on behalf of the Federation of European Biochemical Societies, UK, pp. 149-154.

Tyagi et al., "Extremely sensitive, background-free gene detection using binary proves and QB Replicase," Biochemistry, 1996, 93:5395-5400, Proc. Natl. Acad. Sci. USA, Washington D.C., USA, May 1996.

Tyagi et al., "Molecular Beacons: Probes that Fluoresce upon Hybridization," Nature Biotechnology, 1996, 14:303-308, Nature Publishing Company, New York, USA, Mar. 1996.

Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA, Aug. 1998.

Van Gemen, B. at al.; "The One-tube Quantitative HIV-1 RNA NASBA: Precision, Accurant and Application,"; 1995; *PCR Methods Appl.*; vol. 4; pp. 177-184.

Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.

Voss et al., "Direct genomic fluorescent on-line sequencing and analysis using in vitro amplification of DNA," Nucl. Acids Res., 1989, 17(7):2517-2527, IRL Press, USA.

Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.

Walker et al., "Strand displacement amplification (SDA) and transient-state fluorescence polarization detection of *Mycobacterium tuberculosis* DNA," Clin. Chem., 1996, 42(1):9-13, American Association for Clinical Chemistry, Washington D.C., USA.

Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA, Nov. 1996.

Whelan et al., "The Role of Nucleic Acid Amplification And Detection In The Clinical Microbiology Laboratory," Annu. Rev. Microbiol., 1996, 50:349-373, Annual Reviews, Palo Alto, USA.

Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.

Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.

Wittwer et al., "The LightCycler: a microvolume multisample fluorimeter with rapid temperature control," BioTechniques, 1997, 22:176-181, Informa Healthcare USA, Inc., London, United Kingdom, Jan. 1997.

Yourno et al., "A method for nested PCR with single closed reaction tubes," PCR Methods Appl., 1992, 2(1):60-65, Cold Spring Harbor Laboratory Press, Cold Spring Harbor, New York, USA.

Genprobe; "Test Procedure Guide. AMPLIFIED *Mycobacterium tuberculosis* Direct (MTD) Test,"; 2000, 1 page.

International Search Report and Written Opinion mailed on Nov. 6, 2013 for PCT Patent Application No. PCT/US2012/063918, 22 pages.

ABI Product Catalogue, 1993-1994, "DNA Sequencing Reagents," p. 146, Applied Biosystems, USA.

"GeneAmp optical reaction plate," Nature, 1998, 391(8):210, Nature Publishing Group, USA, from PE Applied Biosystems.

Asper et al., "Laboratory Mechanization and Automation," in Laboratory Organization Automation, 1991, pp. 271-275, Walter deGruyter, USA.

Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.

Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. for Clin. Chem., USA.

Burg et al., "Real-time fluorescence detection of RNA amplified by Q beta replicase," Anal. Biochem., 1995, 230(2):263-272, Academic Press, Orlando, Florida, USA.

Chemistry Guide, "ABI PRISM DNA Sequencing," 1995, pp. 1-3-1-6, The Perkin-Elmer Corporation, USA.

Civitello et al., "A simple protocol for the automation of DNA cycle sequencing reactions and polymerase chain reactions," DNA

(56) References Cited

OTHER PUBLICATIONS

Sequence—J. DNA Sequencing and Mapping, 1992, 3:17-23, Harwood Academic Publishers GmbH, UK.
Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.
Educational Guide, "New Directions in Molecular Diagnostic Testing," pp. 1-12, Rev. A, 2000, Gen-Probe Incorporated, San Diego, USA.
Felder, "Automation of Preanalytical Processing and Mobile Robotics," in Handbook of Clinical Automation, Robotics, and Optimization, 1996, pp. 252-256, John Wiley & Sons, Inc., USA.
Hawkins et al., "Thermal Cycle DNA Sequence Setup Using a Modified Lab Workstation," LRA, 1995, 7:117-122, VCH Publishers, New York City, USA.
Higuchi et al., "Kinetic PCR Analysis: Real-time Monitoring of DNA Amplification Reactions," Bio/Technology, 1993, 11(9):1026-30, Nature Publishing Group, New York, USA, Sep. 1993.
Hill et al., "The Polymerase Chain Reaction in Molecular and Micro-biology," Biotechnol. Genet. Eng. Rev., 1992, 10:343-377, Taylor & Francis, UK, Dec. 1992.
Holmberg et al., "Automatic Preparation of DNA Templates for Sequencing on the ABI Catalyst Robotic Workstation," Automated DNA Sequencing and Analysis, 1994, Academic Press Inc., San Diego, USA, pp. 139-145.
Hunkapiller, "Advances in DNA sequencing technology," Curr. Opin. Genet. Dev., 1991, 1:88-92, Elsevier, UK.
Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.
Kasper, "Automated Instrumentation (Generic)," in Clinical Laboratory Instrumentation and Automation: Principles, Applications, and Selection, 1994, pp. 184-205, W.B. Saunders Company, USA.
Kaufman et al., "Direct Sequencing by PCR," in Handbook of Molecular and Cellular Methods in Biology and Medicine, 1995, pp. 233-235, CRC Press, USA.
Krieg, ed., "Quantitation of RNA Transcripts Using RT-PCR," in A Laboratory Guide to RNA: Isolation, Analysis, and Synthesis, 1996, pp. 176-190, John Wiley & Sons, Inc., USA, article by Ferre' et al.
Little et al., "Recent Advances in Robotic Automation of Microplate Assays," Lab. Info. Mgmt., 1994, 26:89-99, Elsevier Science, Amsterdam, Netherlands.
Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.
Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.
McDomough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.
Mertes et al., Automatische genetische Analytik, 1997, forward and pp. 68, 69, 73 & 74, Wiley-VCH, Germany; German Language Reference.
Mizutani et al., "Magnetic Separation in Molecular Studies of Human Leukemia," in Advances in Biomagnetic Separation, 1994, p. 127-133, Eaton Publishing, USA.
Olsvik et al., "Magnetic Separation in Laboratory Diagnosis of Infectious Diseases," in Advances in Biomagnetic Separation, 1994, pp. 149-158, Eaton Publishing, USA.
Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.

Overbergh et al., "Quantification of Murine Cytokine mRNAs Using Real Time Quantitative Reverse Transcriptase PCR," Cytokine, 1999, 11(4):305-312, Academic Press, USA, Apr. 1999.
Petrik et al., "High throughput PCR detection of HCV based on semiautomated multisample RNA capture," J. Virol. Methods, 1997, 64:147-159, Elsevier/North-Holland Biomedical Press, Amsterdam, Netherlands.
Piatek et al., "Molecular beacon sequence analysis for detecting drug resistance in *Mycobacterium tuberculosis*," Nature Biotechnology, 1998, 16:359-363, Nature America Publishing, New York, USA, Apr. 1998.
Shah et al., "Novel, Ultrasensitive, Q-Beta Replicase-Amplified Hybridization Assay for Detection of *Chlamydia trachomatis*," J. Clin. Microbiol., 1994, 32(11):2718-2724, American Society for Microbiology, USA, Nov. 1994.
Slatko, "Thermal Cycle Dideoxy DNA Sequencing," in Protocols for Gene Analysis (Methods in Molecular Biology), 1994, vol. 31, pp. 35-45, Humana Press Inc., USA.
Sloan et al., "Screening Yeast Artificial Chromosome Libraries with Robot-Aided Automation," GATA, 1993, 10(6):128-143, Elsevier Science Publishing Co., Inc., USA.
Truchaud et al., "Liquid-Phase Reactions Started by Rehydrating Lyophilized Reagents in a Centrifugal Analyzer," Clin. Chem., 1985, 31(9):1506-1508, Am. Assoc. For Clin. Chem., USA.
Tyagi et al., "Multicolor molecular beacons for allele discrimination," Nat. Biotechnol., 1998, 16:49-53, Nature Publishing Group, USA, Jan. 1998.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
Muller et al., "Evaluation des klinish-chemischen Analysensystems Technicon DAX 72," Lab. Med., 1992, 16:210-218, Am. Soc. For Clinical Pathology, USA, with English Summary.
Chinese Office Action mailed on Mar. 24, 2015 for CN Patent Application No. 201280066159.2, with English Translation, 27 pages.
International Search Report and Written Opinion mailed on Aug. 9, 2012 for PCT Patent Application No. PCT/US2012/037585, 10 pages.
Package Insert, "Gen-Probe® Amplified *Mycobacterium tuberculosis* Direct Test," IN0006 Rev. A, Feb. 24, 1994, Gen-Probe Incorporated, San Diego, USA, 14 pages.
Package Insert, "Gen-Probe® Amplified™ Chlamydia Trachomatis Assay," IN0012 Rev. A, Jan. 6, 1997, Gen-Probe Incorporated, San Diego, USA, 17 pages.
Package Insert, "Gen-Probe® Amplified™ Chlamydia Trachomatis Swab Specimen Preparation Kit," IN0016 Rev. A, Jan. 6, 1997, Gen-Probe Incorporated, San Diego, USA, 3 pages.
Package Insert, "Gen-Probe® Amplified™ Chlamydia Trachomatis Urine Specimen Preparation Kit," IN0017 Rev. A, Nov. 11, 1996, Gen-Probe Incorporated, San Diego, USA, 3 pages.
Package Insert, "Gen-Probe® Aptima ® Combo 2 Assay," IN0037 Rev. A, Jun. 6, 2001, Gen-Probe Incorporated, San Diego, USA, 28 pages.
Package Insert, "Gen-Probe® Aptima Combo 2® Assay," 501011 Rev. A, Jan. 2007, Gen-Probe Incorporated, San Diego, USA, 44 pages.
Package Insert, "Gen-Probe® Aptima® Assay for *Chlamydia trachomatis*," IN0147-01, Rev. B, Apr. 2005, Gen-Probe Incorporated, San Diego, USA, 24 pages.
Package Insert, "Procleix® HIV-1/HCV Assay," IN0076-01-FDA, Rev. 3, Jun. 2004, Gen-Probe Incorporated, San Diego, USA, 28 pages.

(56) References Cited

OTHER PUBLICATIONS

Package Insert, "Procleix® HIV-1/HCV Assay," IN0076-02-FDA, Rev. 1, Jan. 2005, Gen-Probe Incorporated, San Diego, USA., 32 pages.
Package Insert, "Procleix® Ultrio™ Assay," IN0167EN, Rev. 1, Aug. 2004, Gen-Probe Incorporated, San Diego, USA, 44 pages.
Package Insert, "Procleix® WNV Assay," IN0155, Rev. 1, Apr. 2004, Gen-Probe Incorporated, San Diego, USA, 15 pages.
Paillard et al., "Direct nucleic acid diagnostic tests for bacterial infectious diseases: Streptococcal pharyngitis, pulmonary tuberculosis, vaginitis, chlamydial and gonococcal infections," MLO, Jan. 2004, pp. 10-15, Medical Laboratory Observer, NP Communications, LLC, Monroe Township, USA.
Panaccio et al., "PCR based diagnosis in the presence of 8% (v/v) blood," Nucleic Acids Res., 1991, 19(5):1151, Oxford University Press, Oxford, United Kingdom.
Chinese Office Action mailed on Nov. 16, 2015 for CN Patent Application No. 201280066159.2, with English Translation, 23 pages.
Japanese Office Action mailed on Sep. 6, 2016 for JP Patent Application No. 2014-540214, with English Translation, 20 pages.

* cited by examiner

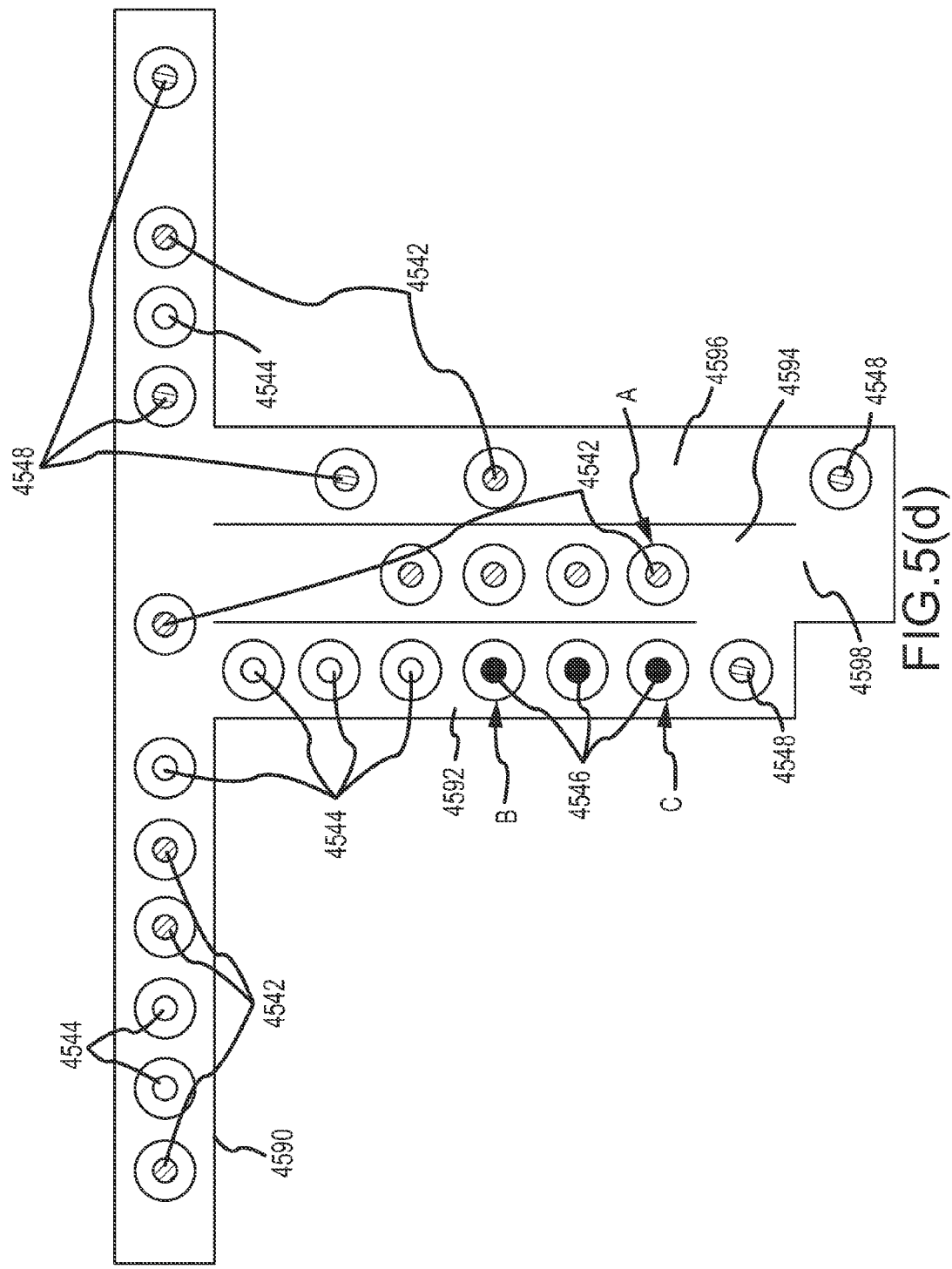

ALIQUOTTER SYSTEM AND WORKFLOW

CROSS-REFERENCES TO RELATED APPLICATIONS

This application claims priority to U.S. Provisional Patent Application No. 61/556,667, filed Nov. 7, 2011 and entitled "Analytical System and Method for Processing Samples." This application also claims priority to U.S. Provisional Patent Application No. 61/616,994, filed Mar. 28, 2012 and entitled "Analytical System and Method for Processing Samples." This application also claims priority to U.S. Provisional Patent Application No. 61/680,066, filed Aug. 6, 2012 and entitled "Analytical System and Method for Processing Samples." All of these applications are herein incorporated by reference in their entirety for all purposes.

BACKGROUND

Conventional medical laboratory systems contain many segments for processing patient samples, some of which are automated and some of which require manual operation. Laboratory systems today have become more efficient due to those segments which have become automated. However, there are still several components of medical laboratory systems that can be automated in order to reduce the time it takes for an analysis of a sample, reduce the need for manual operation of the system, and reduce the space required by machinery.

Generally, the laboratory process can be organized into four phases: association, pre-analytical, analytical, and post-analytical. These four phases typically occur within any laboratory process. However, some conventional labs may have a process that uses standalone units throughout the lab while others may connect some of the units with a conveyance system to move the sample from unit to unit. These two styles have some common and some different processing needs. Additionally, some conventional labs may consistently process the same types of sample tubes (e.g., as in those from a kit) while others may have a wide range of tube types that they must accommodate. Furthermore, many labs may have a preference for a particular manufacturer of an analyzer while others may use all of the analyzers from one manufacturer.

Thus, there is a need for a more efficient system and method for processing patient samples that can accommodate both a process using standalone units and units connected with a conveyance system, a variety of sample tube types, and analyzers from any manufacturer.

Automated laboratory systems may include aliquotter systems. Conventional aliquotter systems typically handle sample tubes via the main transport system of a laboratory automation system. For example, an aliquotter system may transfer liquid from a primary to a secondary tube, both of which are on the main transport system during the aliquotting process. In such a case, once the secondary sample tube is prepared, a laboratory technician must transfer the secondary tube to the desired analysis module. Because the system is not entirely automated, such a process is slow and inefficient.

In another example, a conventional aliquotting system may perform the aliquotting process for sample tubes that are in line with one another. For example, one or more secondary tubes may be directly behind the primary tube on a conveyance system so that the secondary tubes are blocked by the primary tube. Such a system prevents the secondary tube from leaving the aliquotting system until the aliquotting process is finished for all secondary tubes that need to be filled with the sample in the primary tube. The secondary tubes are unable to move on to the next analysis module until all aliquotting for that sample is complete, thereby delaying the entire sample analysis process.

Embodiments of the invention address these and other problems, individually and collectively.

BRIEF SUMMARY

Embodiments of the technology relate to systems and methods for efficiently processing patient samples.

One embodiment of the invention is directed to a system comprising an aliquotter module comprising a track comprising a plurality of loops comprising a first loop configured to hold a secondary sample container and a second loop configured to hold a primary sample container, and a pipettor configured to aspirate a first aliquot volume of a sample in the primary sample container located in an aspiration position and dispense the first aliquot volume of the sample in the secondary sample container located in a dispensing position. The aliquotter module is configured to cause the secondary sample container to leave the aliquotter module before the primary sample container.

Another embodiment of the invention is directed to a method comprising aspirating an aliquot volume of a sample in a primary sample container located in an aspiration position adjacent to a first loop of a track in an aliquotter module, dispensing the aliquot volume of the sample in a secondary sample container located in a dispensing position adjacent to a second loop of the track in the aliquotter module, and causing the secondary sample container to leave the aliquotter module before the primary sample container.

Another embodiment of the invention is directed to a system comprising an aliquotter module comprising a pipettor configured to aspirate a first aliquot volume of a sample in the primary sample container in a first independently movable carrier located in an aspiration position and dispense the first aliquot volume of the sample in the secondary sample container in a second independently movable carrier located in a dispensing position. The aliquotter module is configured to cause the secondary sample container to leave the aliquotter module before the primary sample container.

Another embodiment of the invention is directed to a method comprising aspirating an aliquot volume of a sample in a primary sample container in an independently movable carrier located in an aspiration position adjacent to a first loop of a track in an aliquotter module, dispensing the aliquot volume of the sample in a secondary sample container located in an independently movable carrier in a dispensing position adjacent to a second loop of the track in the aliquotter module, and causing the secondary sample container to leave the aliquotter module before the primary sample container.

Another embodiment of the invention is directed to a system comprising an aliquotter module comprising a first track, a second track, a transport track, a rotatable gateway device proximate the transport track and the first track or the second track, and a pipettor configured to aspirate a first aliquot volume of a sample in the primary sample container located in an aspiration position proximate the first track and dispense the first aliquot volume of the sample in the secondary sample container located in a dispensing position proximate the second track.

Another embodiment of the invention is directed to a method comprising aspirating an aliquot volume of a sample in a primary sample container located in an aspiration position adjacent to a first track of a track in an aliquotter module, dispensing the aliquot volume of the sample in a secondary sample container located in a dispensing position adjacent to a second track of the track in the aliquotter module, rotating a rotatable gateway device; and moving the secondary sample container from the second track to a transport track.

These and other embodiments of the technology are described in further detail below.

BRIEF DESCRIPTION OF THE DRAWINGS

A further understanding of the nature and advantages of the different embodiments may be realized by reference to the following drawings.

FIG. 5(d) shows a top plan view of a third aliquotter module according to an embodiment of the invention. The third aliquotter module comprises linear lanes and independently movable carriers.

DETAILED DESCRIPTION

Embodiments of the present technology relate to a laboratory system and method for processing patient samples. These embodiments, as will be described in more detail below, are advantageous because they provide, among other advantages, greater speed, accuracy, efficiency, and prevention of contamination. As discussed above, many conventional laboratory systems may have a process that uses standalone units throughout the lab, requiring that the samples be manually transported between each standalone unit, while others may connect some of the units with a conveyance system to move the samples from unit to unit. Additionally, as discussed above, sample tube sizes and equipment from different manufacturers may be constraints in conventional laboratory systems. Such conventional technology is slow and inaccurate. Embodiments of the present technology provide for a modular laboratory system which is capable of accommodating different laboratory units and transport systems, sample tube sizes, and manufacturers by using more universal components and by grouping functions required by most laboratory systems into five basic functional units: (1) manager, (2) centrifuge, (3), aliquotter, (4) output/sorter, and (5) storage units. These five basic functional units will be described in more detail below.

In embodiments of the invention, the laboratory system operates a controlled process using a central controller or scheduler. By keeping the samples under the control of an intelligent scheduler, the system provides for efficient usage of every instrument. The system can maintain a consistent minimal turnaround time and maximizes the throughput of the entire system by maintaining control of the process and only delivering samples to instruments when those instruments are ready and available.

In embodiments of the invention, a "sample container" may have any suitable shape or form. In some embodiments, the sample container may be in the form of a sample tube, which may have an aspect ratio of greater than about 3:1. Such sample containers may be made of any suitable material including plastic, glass, etc. They may further include a sample tube body with a closed end and an open end, as well as a cap that is structured to cover and attach to the open end of the sample tube body.

I. Overall System

A. Phases of Laboratory System

Figure 1:
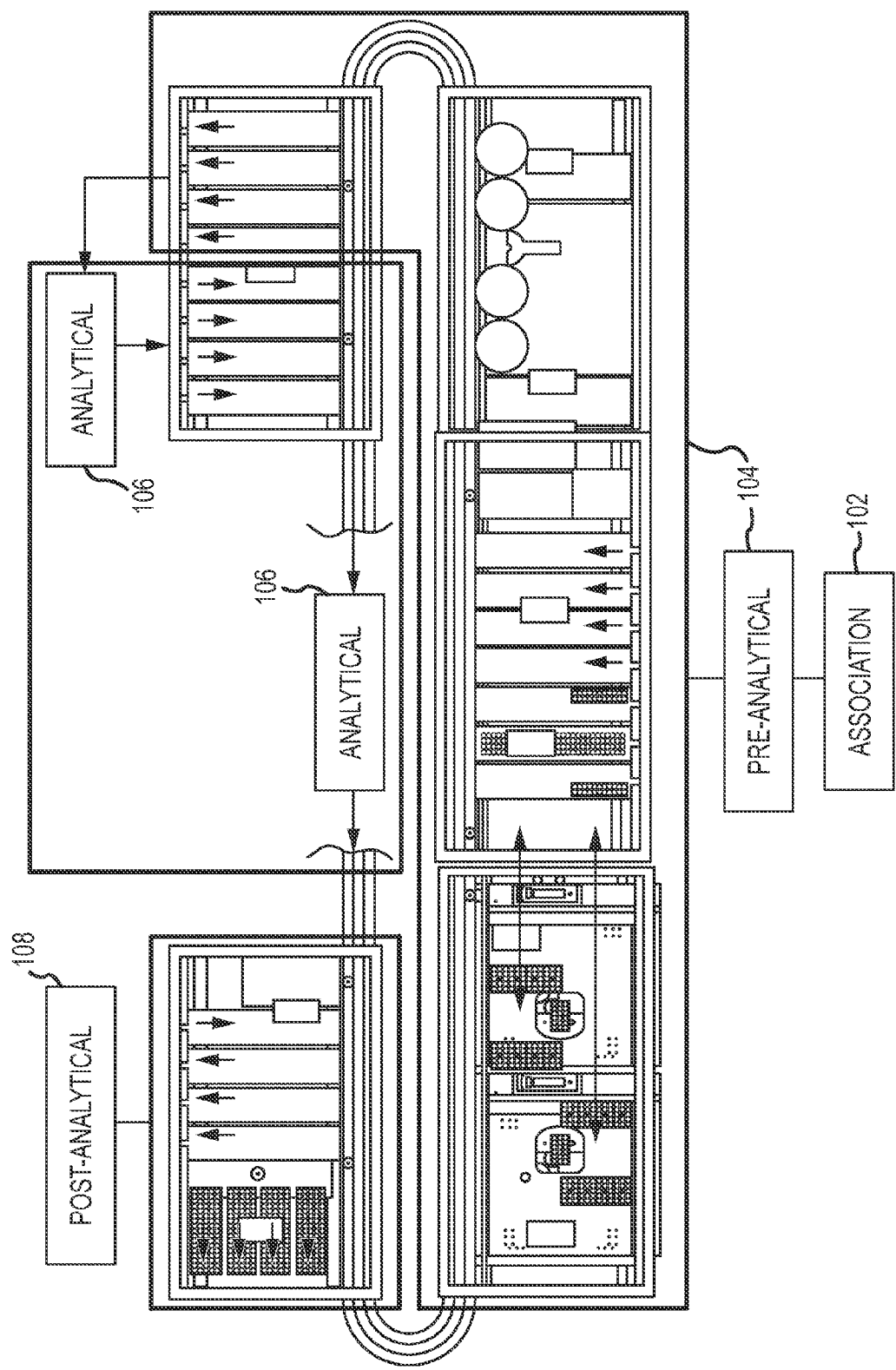
FIG. 1 depicts a block diagram of components associated with phases of a laboratory automation system.

FIG. 1 depicts one embodiment of a medical laboratory system for processing patient samples. The laboratory system includes components associated with the association phase 102, the pre-analytical phase 104, the analytical phase 106, and the post-analytical phase 108.

1. Association Phase

The association phase 102 is the first phase in the laboratory process. During this phase, the patient information, the requested tests for the patient sample, and a unique laboratory identifier (e.g., a barcode) are associated with one another. While the association phase 102 could be automated, in some embodiments, the association phase is handled manually. For example, in some embodiments, a laboratory technician (hereinafter referred to as a "user") can assign a priority to the samples. The samples are loaded into racks or directly onto the system at specific entry points. Although grouping samples into a few basic priority levels (e.g., urgent or high priority, medium priority, low priority, etc.) may be desirable to provide a more consistent turnaround time, it is not necessary. Processing patient samples can be based on any priority defined by the user. However, if a priority is not specified, a priority can be assigned based on factors such as minimizing turnaround time, maximizing throughput, the availability of processes, etc.

2. Pre-Analytical Phase

The pre-analytical phase 104 includes preparing patient samples for analysis. During the pre-analytical phase 104, the patient and test information is deciphered, the process for analysis is planned, quality checks are performed, the sample may be separated into its constituent components (e.g., centrifuged), the sample may be divided for parallel analytical processes, and/or the sample can be delivered to one or more analyzers and/or racks. The pre-analytical phase 104 manages the flow of samples to different instruments and different analyzers within the lab system. This process management permits the system to operate efficiently and with minimal instruments. Additionally, the pre-analytical phase 104 ensures that a backup of patient samples at different points within the lab system does not occur along the process, or if a backup does occur, the pre-analytical phase 104 ensures that the backup can be cleared quickly and without significant impact on the remainder of the system.

Embodiments of the system can identify the patient samples as quickly as possible and determine the best scheduling of each sample to provide a consistent, minimal turnaround time and maximum throughput of the analytical processes. The steps and organization of those steps in the process are designed to avoid backups of patient samples. Modules of the lab system can operate at a throughput speed that ensures processing of samples at the maximum throughput of the upstream processes. However, in some embodiments, at the aliquotter unit, the throughput may be managed by the introduction of samples upstream and by small queues at each aliquotting station.

Figure 2:
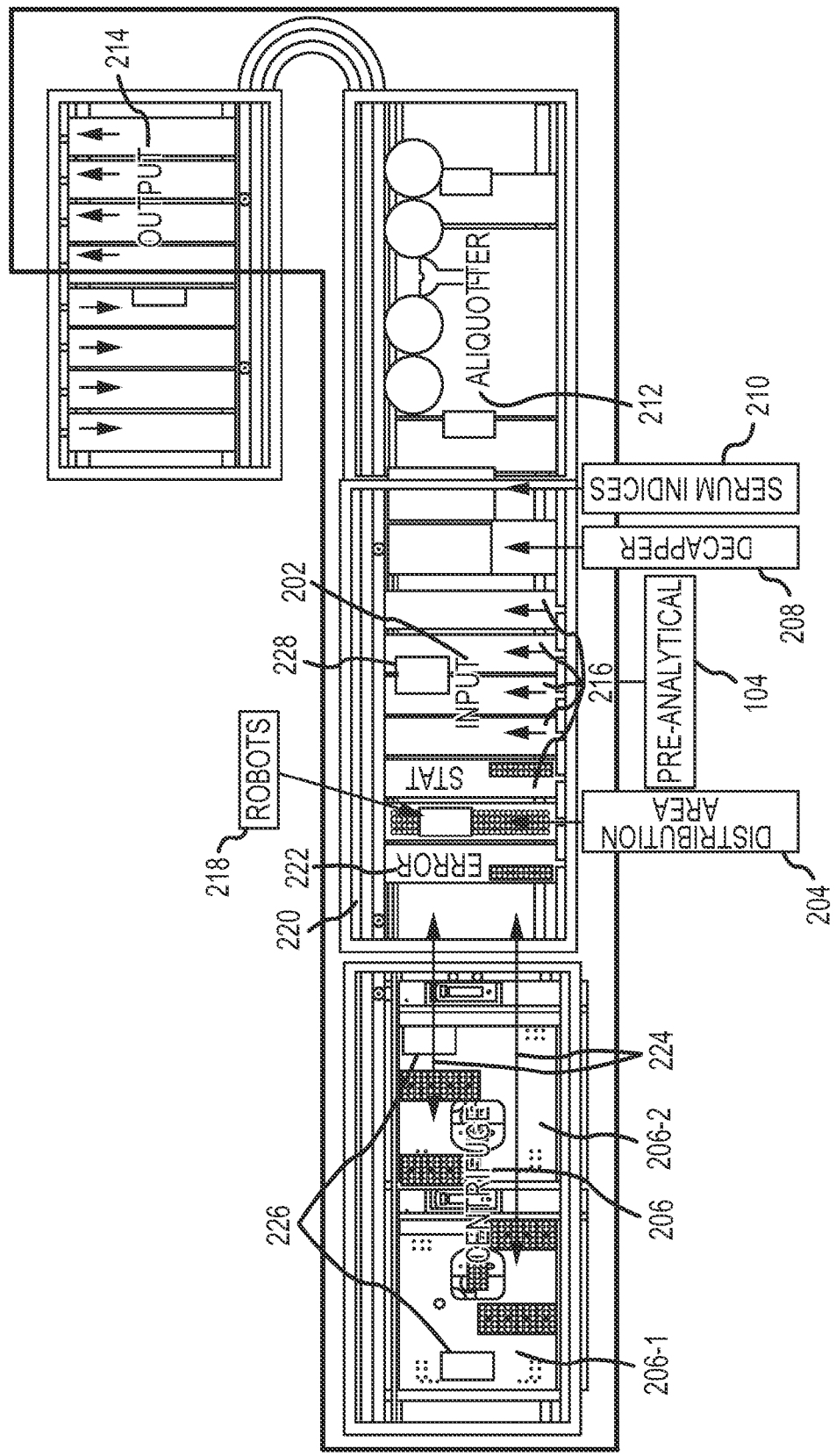
FIG. 2 depicts a block diagram of components associated with a pre-analytical phase of a laboratory automation system.

FIG. 2 is a more detailed depiction of the components associated with the pre-analytical phase 104. The components associated with the pre-analytical phase 104 include seven modules: input module 202, distribution area 204, centrifuge 206, decapper 208, serum indices measurement device 210, aliquotter 212, and output/sorter 214.

(a) Input Module

The input module 202 shown in FIG. 2 can accommodate a variety of tubes, racks, prioritizations, etc. and is capable of receiving a specimen. Racks of tubes and/or individual tubes can be loaded onto one of several lanes 216, which may be manually operated drawers and/or automated devices. In FIG. 2, five lanes 216 are depicted. However, the lab system can have any number of lanes 216. The lanes 216 are assigned priorities in accordance with those assigned by the user. In some embodiments, the highest priority lane (short turnaround time or "STAT") may have a fixed position for accepting a group of individual tubes from the user. Once tubes are loaded in the STAT lane, they become the next tubes processed. Other lanes can be assigned different priority levels in any manner. For example, when the drawers are manually operated, assigning one priority to at least two of the drawers and another priority to at least two other drawers may allow the system to operate continuously on one drawer while the other drawer of the same priority is available to the user.

In some embodiments, while the input module 202 is processing a drawer of samples, the user may be informed that the drawer should not be opened by using an indication such as a light on the drawer or a lock on the drawer. This may help maintain the process integrity and maximize throughput. When processing is complete on the first drawer, the drawer may be identified to the user as available, and the system may automatically begin processing another drawer. Additionally, the samples can be transferred to and from the drawers 216 of the input module 202 using an input module gripper 228.

(b) Distribution Area Module

From the lanes 216 within the input module 202 of FIG. 2, a distribution area gripper 218 (discussed in more detail below) may select the highest priority tube and transport it to a fixed matrix called the distribution area 204. The distribution area 204 is capable of distributing a specimen to a desired component of the laboratory automation system. During the transfer to this module by the input module gripper 228, the levels of the sample's constituent components are measured and photographs of the sample tube are taken. These photographs can be analyzed to determine the tube's manufacturer, diameter, height, cap color, etc. From this information, the volumes of the sample's components can be calculated, and an estimate of the total tube weight can be made. This weight can be later used to aid in balancing the centrifuge buckets in the centrifuge module 206, as will be discussed in more detail below.

To protect the distribution area 204 from filling with low priority tubes, a limit can be set on the number of tubes loaded into this area from the low priority input lanes. Moreover, the distribution area 204 may have a reserved area to ensure STAT samples have continuous access to the distribution area 204 from the STAT drawer in the input module 202.

The distribution area 204 can be the holding area which permits the system to access test information associated with the sample tube in the association phase 102 and plan the analysis process for the sample. This enables the system to schedule a sample tube's process with respect to the other sample tubes currently on the system. Scheduling enables the efficient processing of samples based upon priority without overloading any step in the overall system, permitting the optimization of turnaround time and throughput. Furthermore, the sample's schedule can be updated throughout the process as the system's activity or availability changes, providing real time active control of the sample.

Once the schedule is planned by the distribution area module 204, the robotic gripper 218 then selects the sample tube that is the next tube to be transferred to the next module based on the priority of the tubes within the distribution area 204. The selected sample tube is transported from the distribution area 204 to the conveyance system 220, to the centrifuge module 206, or to an output drawer with an error area 222 based on the analysis performed by the distribution area module 204.

If the sample tube is being moved to the centrifuge module 206, the tube can be placed into the appropriate centrifuge adapter based upon the earlier weight estimation to ensure proper balance of the centrifuge rotor. The centrifuge adapter is the component which carries the tubes upon a shuttle from the distribution area 204 to the centrifuge whereupon a robotic gripper transfers the centrifuge adapter with the tubes to a bucket of the centrifuge.

If the distribution area module 204 determines that the sample tube does not require centrifugation, the distribution area robot gripper 218 places the sample into a carrier on the conveyance system 220 with the barcode label properly aligned to the carrier at the direction of the scheduler so as not to overload downstream processes. More details on the conveyance system 220 and the carriers will be discussed below. A carrier can refer to any suitable device, which can be present in a conveyance system and can carry or transport one or more sample containers or tubes. Exemplary carriers may contain recesses which can hold the containers or tubes. If a problem exists with the sample (e.g., the volume is too low, the barcode is unreadable, no test information is downloaded, etc.), the sample tube is moved to the error area 222 and the user is notified of the issue.

(c) Centrifuge Module

The sample tube may be moved from the distribution area 204 of FIG. 2 to the centrifuge module 206 if the distribution area module 204 determines that the sample requires centrifugation before analysis of the sample. When a sample tube is to be transported from the distribution area 204 to the centrifuge module 206, the sample tube is loaded by the distribution area robot gripper 218 into a centrifuge adapter at the distribution area 204. The adapters may locate and retain multiple tube sizes for centrifugation. The adapter sits in a shuttle 224 which moves between the distribution area 204 and the centrifuge module 206 once the adapter is filled with sample tubes. An adapter can be a device which holds sample containers, and can be used in a centrifuge. Such adapters are commonly constructed of a polymeric material but not limited to and constructed as a single piece having a shape which allows retention of one or more containers in which a sample may be placed. In some cases, an adapter is inserted into a device mounted on or in a centrifuge rotor. Labware (e.g., sample containers or tubes) holding the sample is inserted in the adapter.

When the sample tubes in the adapters arrive at the centrifuge module 206 from the distribution area 204 via the shuttle 224, the adapters are loaded into an available centrifuge bucket. The configuration of the adapters allows for simplification of delivery to and removal from the centrifugation buckets. Once loaded into a centrifuge bucket, the samples can be centrifuged. The centrifuge module 206 may include one or more centrifuges that are refrigerated to maintain the temperature of the sample. In FIG. 2, two centrifuges 206-1 and 206-2 are depicted. The centrifuges use a swinging centrifuge bucket rotor which produces level sedimentation layers from which analyzers and pipettors can consistently aspirate the maximum volume of fluid. Once centrifugation is complete, the adapters can be removed from the centrifugation bucket and placed in an unloading area. The sample tubes are then removed from the adapters in the unloading area and placed in carriers on the conveyance system 220 for transport to the next module.

The timing for loading tubes into an adapter at the distribution module 204, sending the tubes in the adapter to the centrifuge module 206 via the shuttle 224, loading the adapter into a centrifuge bucket, centrifuging the samples, unloading the adapter from the centrifuge bucket, and unloading the tubes from the adapter is such that the process is continuous, allowing for the continual centrifugation of samples as they arrive at the centrifuge module 206 from the distribution area 204. As the centrifuge completes a spin cycle, the last tube in the distribution area 204 is loaded by the distribution area gripper 218 into an adapter, and the shuttle 224 moves the adapter to a centrifuge in the centrifuge module 206. At the same time, an automated door on the centrifuge opens and provides access to a bucket as the rotor indexes into position at the doorway. A centrifuge module gripper 226 in the centrifuge module 206 removes the adapter that is already in the bucket and moves that adapter to an area where the tubes will be unloaded to carriers on the conveyance system 220. Next, the centrifuge module gripper 226 selects an adapter that has been recently loaded with tubes from the distribution area 204 and deposits it into the empty bucket. While the rotor indexes to the next bucket, a previously emptied adapter is moved to the open position on the shuttle 224 for loading with tubes from the distribution area 204 when the shuttle 224 returns to the distribution area 204.

After the final adapter is loaded into the centrifuge, the door closes and the spin cycle begins. The adapter shuttle 224 moves back to the distribution area 204, and a centrifuge module gripper 226 begins to unload tubes from the adapters removed from the buckets into carriers on the conveyance system 220. As the tubes are moved from the adapter to the carrier, the heights of the sedimentation layers are measured and the barcode on each tube is aligned with the carrier. If insufficient serum or plasma is present, the tube will be sent to an error area located in the output module 214.

If the scheduling algorithm predicts the overloading of an analyzer with samples from the centrifuge module 206, the centrifuge module gripper 226 can unload the samples and distribute the samples from the adapters to the conveyance system. In some embodiments, the full cycle time of the centrifuges can be greater than or equal to, e.g., 360 seconds. In order to ensure optimal TAT and throughput the centrifuges are kept, e.g., 180 seconds out of phase for a 360 seconds centrifugation cycle. In some embodiments, downstream processes do not prevent the unloading of samples from the centrifuge adapters. If all the remaining samples in an adapter are destined for unavailable process(es) and depending upon the unavailable process, sample tubes can either be moved to a buffer in the centrifuge instrument or moved to another buffer area elsewhere in the system.

The centrifuge module 206 may include an automated centrifuge controlled by a centrifuge controller. The automated centrifuge can be loaded with multiple centrifuge buckets or receptacles, each bucket receiving multiple sample tubes. The centrifuge includes a motor coupled to a spindle, a rotor assembly, a controller, a lid, and optionally, a lid drive. The centrifuge controller indexes or stops the spindle at selected positions for automated placement and removal of either tubes, adapters or buckets. The lid has a closed position and an open position, and the lid opens and closes in response to instructions from the centrifuge controller.

In some embodiments, before the loaded buckets are placed in the centrifuge, the buckets can be balanced in a balance system. The balance system, which can be an included part of the centrifuge module 206, comprises a scale having sites for receiving and holding a plurality of buckets, and a balance controller for selectively depositing sample tubes in cavities of the buckets while correlating incremental weight changes with the locations of each deposit for equalizing weight in pairs of the buckets. The balance controller can be implemented as a balance program within the central controller. The balance program maintains a database of sample container weights. When a container's weight is combined with the sample's weight, the balance program can determine the optimum adapter cavity in which to place it thereby maintaining a balanced rotor within a tolerance. Sample weights are the product of density estimates and the sample volumes calculated from liquid level measurements and container geometry obtained during the initial pick-up from the input. In some embodiments, balance system may also include a supply of dummy loads in buckets for limiting weight variations between buckets. The dummy loads may be weighted for limiting the weight variations to not greater than, e.g., 10 grams between members of each pair of buckets.

In other embodiments, a scale need not be used. For example, in some embodiments, the weight of a sample container and a sample can be estimated, and the adapters can be automatically loaded to ensure a balanced rotor. In some cases, a picture of a sample tube may be taken, and the liquid level of a sample in the sample tube can be determined. Using information about the sample container (e.g., the sample container weight) and the determined liquid level, the weight of the sample tube with the sample in it can be estimated. In such embodiments, a scale is advantageously not needed. Further dummy loads may also not be needed.

The centrifuge controller may operate to perform a number of functions, such as receiving and storing a centrifuge spin profile including a rotor spindle speed and duration, indexing the rotor's sample stations into an access position, spinning the rotor in accordance with the cycle profile, stopping the rotor with a predetermined sample station at the access position, etc.

(d) Decapper Module

The decapper module 208 of FIG. 2 is capable of decapping the cap from the sample tubes in carriers on the conveyance system 220 before they are analyzed. The decapper system may clamp a sample tube and remove the cap from a sample tube. The decapper module 208 follows the distribution module 204 and the centrifuge module 206. For sample tubes which do not require cap removal (e.g., for instances in which the samples may only require sorting), the carrier on the conveyance system 220 will bypass the decapper module 208. For sample tubes that require cap removal, the decapper module 208 may remove the cap from the sample tube and deposit the cap in a biohazardous waste disposal container below the deck of the decapper module 208. The biohazardous waste disposal container is removable and replaceable to protect the user from biohazardous waste.

(e) Serum Indices Module

The serum indices module 210 of FIG. 2 is capable of measuring the serum index of a sample. Typically, this function is performed during the analytical phase 106. However, in some instances, certain laboratories may prefer to address any quality issues prior to delivering the samples to the analyzer. Thus, the serum indices module 210 provides this quality control option for samples that should be tested. For samples that do not require a serum index measurement, the sample may bypass the serum indices module 210.

The serum indices module 210 can be the next module after the decapper module 208 since a serum indices measurement typically requires access to the sample. Similar to the decapper module 208, the serum indices module 210 may have a biohazardous waste disposal container below the deck of this module. The container may be removable and replaceable to protect the user from biohazardous waste.

(f) Aliquotter Module

Figure 3:
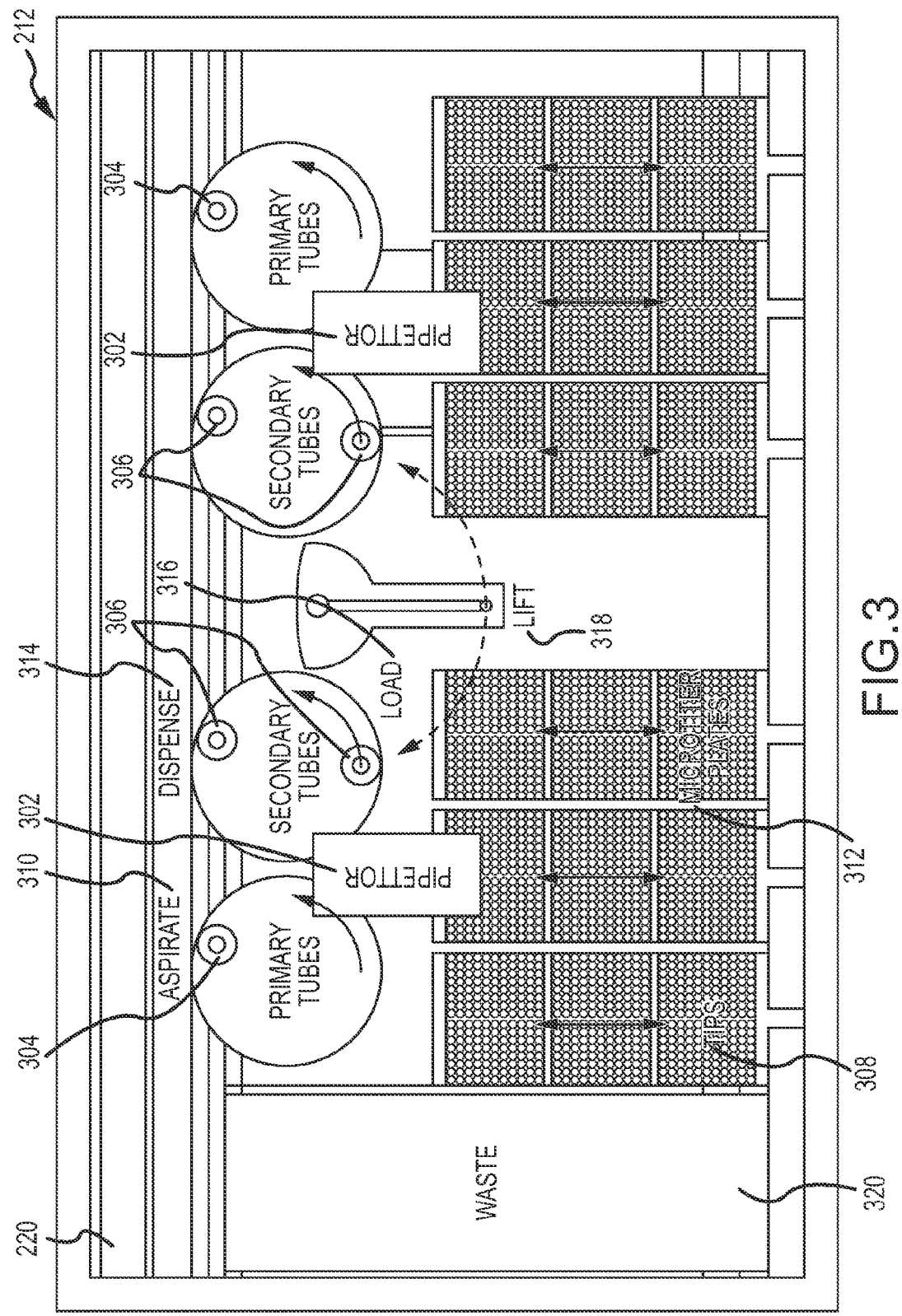
FIG. 3 depicts a block diagram of components within an aliquotter module.

The aliquotter module 212 of FIG. 2 is depicted in greater detail in FIG. 3. The aliquotter module 212 divides the primary sample in sample tubes 304 into multiple secondary sample tubes 306 depending on how many tubes are needed for analysis. This module may contain one or more pipettors 302 for dividing the samples in the primary sample tubes 304 into sample aliquots for secondary sample tubes 306.

As shown, the primary and secondary sample tubes 304, 306 may be on respective rotatable wheels so that they can be removed and/or introduced to the conveyance system 220. The pipettors 302 can be between respective pairs of adjacent rotatable wheels containing the primary and secondary sample tubes 304, 306. As shown, the configuration of the components of the aliquotter module are such that the secondary sample tubes 306 containing sample aliquots can leave the aliquotter module via the conveyance system 220, before the primary sample tubes 304 leave the aliquotter module.

The aliquotter module 212 further facilitates labeling of the secondary sample tubes 306 with a barcode label specifying the patient and test information. The barcode labels are attached to the secondary sample tubes 306 below the deck of the aliquotter module 212 in a device called the Secondary Tube Preparation Unit (STPU). The STPU can produce labeled tubes for one or more pipettors. New secondary sample tubes can be delivered to the aliquotter module 212 in racks and loaded into drawers below the aliquotter module 212. The labels are delivered on a roll and printed below the deck of the aliquotter module 212 prior to attachment to the tubes.

To minimize contamination of patient samples, the pipettors 302 use disposable tips 308. These tips arrive in racks which are loaded into drawers on the deck. The pipettor 302 loads a disposable tip from these racks, aspirates 310 the sample from the primary tube 304 and dispenses 314 the sample into one or more secondary tubes 306 and/or a microtiter plate 312. In one embodiment, the tip may be limited to a particular amount (e.g., 1 milliliter) of the sample. In such a case, dispensing volumes exceeding that particular amount may require multiple aspirations. Once the pipetting is finished for a sample, the tip can be disposed in the waste container 320.

In order to manage the tubes during aspiration 310 and dispensing 314, the primary 304 and secondary 306 tubes are removed from the travel lane of conveyance system 220 and queued on supplementary lanes. Because the aliquotter module 212 may operate at a slower rate than the other modules, the queues minimize the effect of aliquotting on the remainder of the system. Although the queuing process may vary depending upon the conveyance system 220, in this embodiment the carriers with the primary tubes 304 are transferred to a queue wheel. Empty carriers for the secondary tubes 306 are transferred to a separate queue wheel adjacent to the primary tubes 304. The labeled secondary tube 306 is loaded 316 into the empty carrier from below the deck by a lift 318 which rotates around to align with the empty carrier. The STPU transfers the tube to the lift 318 in the correct orientation to ensure the barcode is aligned properly with the carrier. In the case of an aliquotter module 212 having more than one pipettor, the lift 318 rotates the opposite direction to place the tube in the carrier (rotatable wheel).

(g) Output/Sorter Module

The output/sorter module 214 transfers tubes to and/or from racks located in drawers or bays. The output/sorter module 214 can also function as a component for handling the output of the pre-analytical phase 104 and can also function as a sorter for sorting tubes based on the type of analysis that the samples are to undergo. The output/sorter module 214 includes areas to load and/or unload racks of tubes. Additionally, some of the drawers on the output/sorter module 214 may be specified as input and some as output. In the sorter mode, the units with a single robotic gripper select a tube from an input drawer, read the barcode, measure the height of the constituent sample components, take a photograph of the tube and analyze the data to record its manufacturer, diameter, height, and cap color. Based upon the information received from the laboratory information system (LIS), the gripper deposits the tube in the correct rack while aligning the barcode as appropriate. If an error condition is identified, the tube is placed into an error rack.

3. Analytical Phase

Referring again to FIGS. 1 and 2, the analytical phase 106 includes performing the actual measurements needed to process a sample and produce results. This phase is typically composed predominantly of one or more analysis instruments or analyzers. The analysis instruments or analyzers can be any analysis instruments or analyzers known in the art. Typically an analyzer may comprise a mechanism for selectively performing one or more types of analyses on a specimen. The analyzer's controller is in communication with the central controller, so that the central controller can instruct the analyzer controller as to what analysis to perform for the specimen. Each analyzer's controller may also communicate analysis results to the memory of the central controller.

For a laboratory system that has the components associated with the pre-analytical 104, analytical 106, and post-analytical 108 phases connected together via a conveyance system 220, the samples may move past the output/sorter module 214 and onto analyzers. When the carrier reaches the destination analyzer for that particular sample, the carrier pulls off the main travel lane and forms a queue upstream of the analyzer's access point to the conveyance system 220. The queue length is minimal because of the planning done by the scheduler while the tube was still in the distribution area 204 and because of the controlled release of tubes by the distribution 204 and centrifuge 206 modules.

4. Post-Analytical Phase

The final phase of the laboratory process is the post-analytical phase 108. In this phase, the sample is prepared for storage and is stored. Once the sample has completed the testing and analysis required, the sample is capped and placed into storage. This may be either ambient or refrigerated storage depending upon the sample and the laboratory process. Moreover, users with systems having connected analyzers may desire a connected cold storage for some samples and offline ambient storage for others. However, users with unconnected analyzers will likely store all of their samples offline.

II. Aliquotting Module for Various Sample Transportation Systems

As discussed above, the aliquotter module is used in the preparation of sample aliquots from primary into secondary tubes in a laboratory automation system. During the aliquotting process for the preparation of sample aliquots, a primary sample tube containing a fluid sample is provided at an aspiration position. An empty secondary sample tube is provided at a dispensing position. A pipettor, which may be attached to a moveable robotic arm, is used to aspirate an aliquot volume of the fluid sample. The aspirated volume is then transferred to the dispensing position by use of the robotic arm, and the aspirated volume is dispensed in the empty secondary tube. This process can be repeated for additional empty secondary tubes if more sample aliquots are needed.

The aliquotter module of the present technology allows queuing of secondary tubes localized before the primary tubes, relative to the moving direction of the laboratory automation system sample container handling unit. That is, the secondary tubes may leave the aliquotter module as soon as the fluid sample is dispensed in the secondary tube, without having to wait for the aliquotting of that sample to be completed for additional secondary tubes.

The configuration of the aliquotter module is advantageous since the secondary tubes can be released from the dispensing position immediately after the dispensing step and can be directly transferred to the designated target positions in the laboratory automation system, while further aliquots can be produced. Additionally, any number of secondary sample tubes can be consecutively generated from the provided primary tube. This reduces the turn-around-time of a sample in the laboratory automation system and generates a homogenous and optimized load of the transport system and subsequent process steps.

A number of specific embodiments that are described below refer to "pucks" as examples of carriers. It is understood that embodiments of the invention are not limited to pucks, but the carriers according to embodiments of the invention may be in any suitable form.

Figure 4:
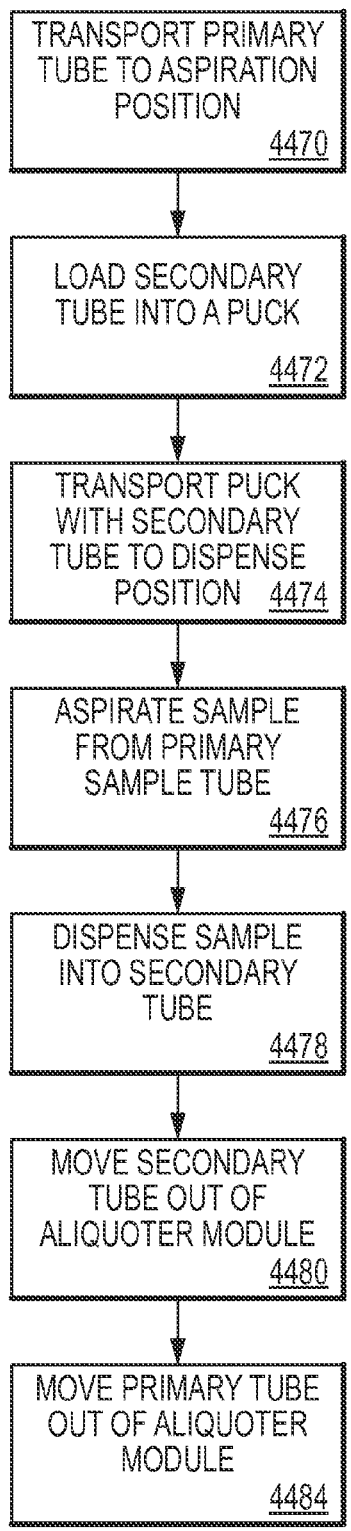
FIG. 4 depicts a flowchart according to an embodiment of the invention.

FIG. 4 shows a flowchart that can illustrate a method of operating an aliquot module according to an embodiment of the invention. It is understood that embodiments of the invention are not limited to the specific steps shown in FIG. 4 or are limited to any particular step order. Further, a computer readable medium in a computer may comprise code, executable by a processor in the computer to execute any of the steps in FIG. 4 or described in this application.

In step 4470, a primary tube is transported to an aspiration position in the aliquotter module. In some embodiments, the primary tube is transported to the aspiration position in a first puck. The primary tube may be transported to the aspiration position using any suitable transport system including pucks on tracks, magnetic pucks, gripper units, etc.

In step 4472, before or after the primary tube is transported to the aspiration position, a secondary sample tube is loaded into a second puck. The puck with the secondary sample tube is then transported to a dispense position in the aliquotter module (step 4474).

In step 4476, an aliquot volume of a sample in a primary tube located in an aspiration position is aspirated by a pipettor. The aliquot volume of the sample is dispensed in the secondary sample tube located in a dispense position in the aliquotter module (step 4478).

In step 4480, the secondary sample tube in the second puck then leaves the aliquotter module before or after the primary sample tube leaves the aliquotter module (step 4484).

Additional sample aliquots may be taken from the primary tube and dispensed into other secondary tubes in a similar manner as in steps 4472 to 4484.

One embodiment of the invention is directed to an aliquotter module comprising a track comprising a plurality of loops comprising a first loop configured to transport a secondary sample container and a second loop configured to transport a primary sample container, and a pipettor configured to aspirate a first aliquot volume of a sample in the primary sample container located in an aspiration position and dispense the first aliquot volume of the sample in the secondary sample container located in a dispensing position. The aliquotter module is configured to cause the secondary sample container to leave the aliquotter module before the primary sample container.

Figure 5A:
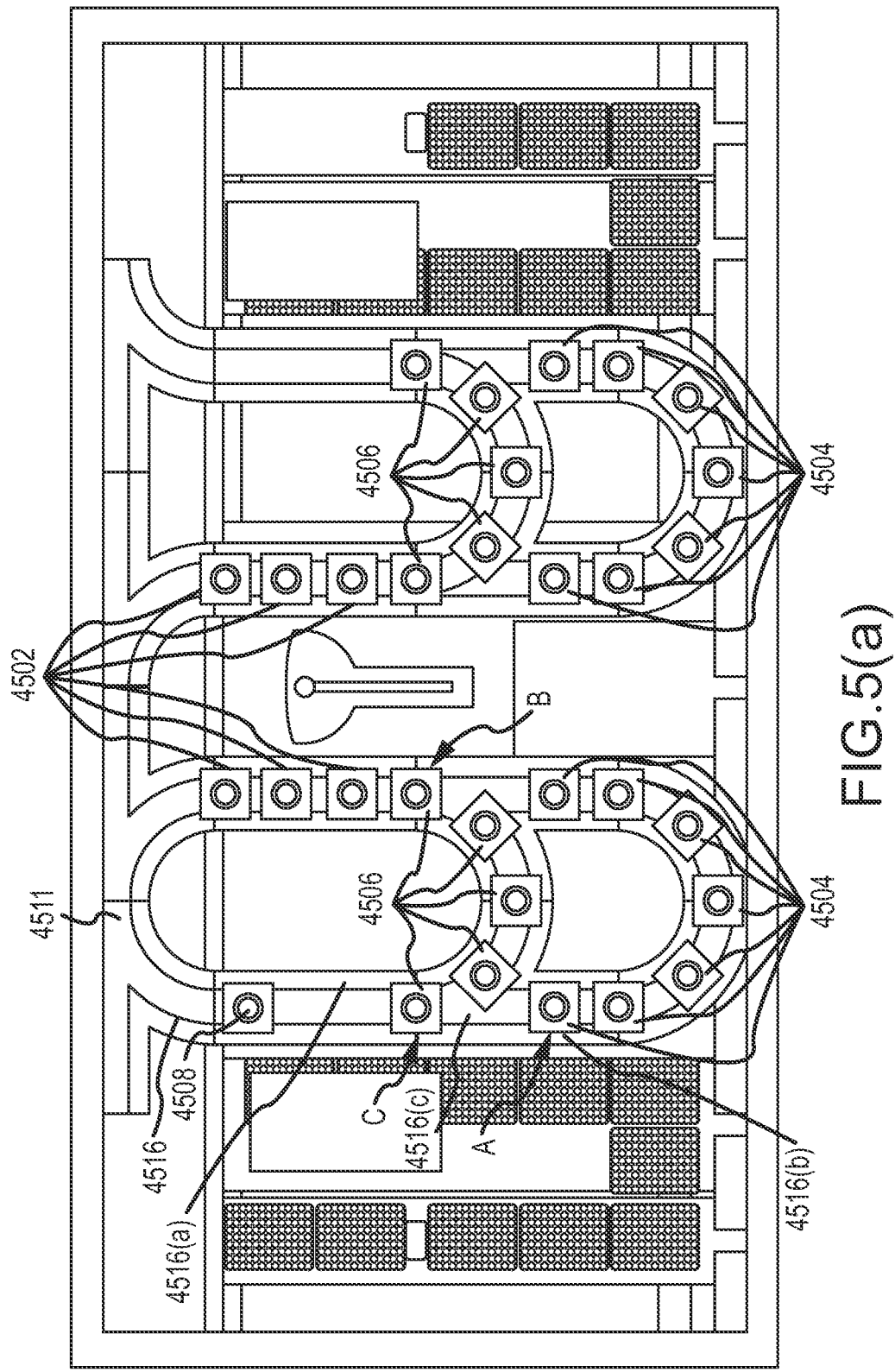
FIG. 5(a) shows a top plan view of a first aliquotter module according to an embodiment of the invention. The first aliquotter module comprises a number of looped lanes.

In one embodiment, an aliquotter module can utilize a magnetic transport system. FIG. 5(*a*) depicts an example of a workflow for an aliquotter module using the magnetic transport system.

The aliquotter module shown on FIG. 5(*a*) comprises a track 4516 including a first loop 4516(*a*), a second loop 4516(*b*), and a common track portion 4516(*c*) that is included in both the first and second loops 4516(*a*), 4516(*b*). The track system may comprise magnetic elements that interact with magnetic elements in a number of pucks. The pucks can move at speeds in the range of up to 2 meters per second, which is faster than standard conveyors. Such tracks are commercially available under the tradename Magnemotion™.

FIG. 5(*a*) shows a number of pucks in the aliquotter module. They include empty pucks 4502, pucks with primary tubes 4504, and pucks with secondary tubes 4506. A puck with a secondary tube 4508 filled with an appropriate aliquot of a sample from a primary tube is also shown. As shown, the various pucks can travel clockwise around the loops 4516(*a*), 4516(*b*) and may exit the aliquotter module via a linear track 4511, also referred to herein as a travel lane. In other embodiments, the pucks could move in a counterclockwise direction.

In an exemplary method of operating the aliquotting module, a primary tube 4504 is identified by the system on the main track for aliquotting and is directed to the aliquotter's aspiration point (A) proximate the second loop 4516(*b*), adjacent to the merge of the loops 4516(*a*), 4516(*b*). The empty pucks 4502 are sent by the system behind the primary tube to the aliquotter's loading point for secondary tubes (B), proximate the loop 4516(*a*). A secondary tube is labeled and loaded into the empty puck 4506 at the aliquotter's loading point for secondary tubes (B) and is directed to the dispensing point (C). The sample is then aspirated from the primary tube 4504 at (A) and dispensed into the secondary tube in the puck 4506 at point (C), proximate to the first loop 4516(*a*). Barcode readers (not shown) at points (A) and (C) verify the correct association by reading barcodes on the sample tube at points (A) and (C). When the secondary tube is complete 4508, it is released to its next destination by entering the linear track 4511 and the next secondary tube moves to the dispensing point (C).

The process can then be completed for any number of additional secondary tubes if the system further routes empty pucks to the aliquotter module. When the last secondary tube is finished, both the last secondary tube and the primary tube are released to their next destinations according to the scheduler, and the trailing secondary and primary tubes are moved to the dispensing (C) and aspiration points (A), respectively. The process can then be completed for the trailing secondary and primary tubes.

The looped track configuration has a number of advantages. They include the ability to continuously and efficiently feed pucks to aspiration and dispense points in an aliquotter module, thereby resulting in faster processing.

Another embodiment of the invention is directed to a system comprising an aliquotter module comprising a first track, a second track, a transport track, a rotatable gateway device proximate the transport track and the first track or the second track, and a pipettor configured to aspirate a first aliquot volume of a sample in the primary sample container located in an aspiration position proximate the first track and dispense the first aliquot volume of the sample in the secondary sample container located in a dispensing position proximate the second track.

In another embodiment, an aliquotter module is utilized with a conveyor transport system, as described above. FIG. 5(*b*) depicts an example of a workflow for an aliquotter module using the conveyor transport system. The aliquotter module comprises a conveyor 4588 which can transport pucks with primary tubes 4522 as well as pucks with secondary tubes with sample aliquots 4528. The system may also comprise a lane or conveyor with empty pucks 4524.

A number of circular tracks may be present in the aliquotter module. Such tracks may comprise a first circular track 4525 for transporting pucks with primary sample tubes and a second circular track 4527 for pucks that are empty 4524, pucks with empty secondary tubes 4526, and pucks with secondary tubes with sample aliquots 4528. Although the tracks 4525 and 4527 are circular in FIG. 5(*b*), tracks with any other configuration can be used. In some cases, the tracks can be in the form of endless loops (e.g., circles, ovals, etc.). As seen in FIG. 5(*b*), the first and second circular tracks 4525, 4527 have no common track portion with the main track 4588.

In the area of the first circular track 4525, a barcode reader 4523 may be present to read a barcode on a sample tube at an aspiration point (A), adjacent to track 4525. A puck manipulator 4584 may also be present at the aspiration point A to control the movement of a puck at aspiration point (A).

In the area of the second circular track 4527, a first barcode reader 4568 and a puck manipulator 4566 may be present to read a barcode on a secondary tube at a loading point (B) (adjacent to track 4527) for secondary tubes. Also in the area of the second circular track 4527, a second barcode reader 4529 and a second puck manipulator 4574 may be present at a dispensing point (C), adjacent to track 4527. The puck manipulators 4523, 4566, 4574 can be in the form of pivoting angular structures that allow a puck to stop or pass so that an operation can be performed on a sample tube in the puck (e.g., aspiration or dispense, or read a barcode on the sample tube).

The various tracks shown in FIG. 5(*b*) may utilize any suitable transport technology including a conveyor system sold under the tradename FlexLink™. The conveyor systems are based on a close-fitting, multiflex plastic chain conveyor that gives a straight, horizontal and vertical running capability.

A first rotatable gateway device 4530 may be adjacent to the linear track 4588 and the first circular track 4525. The first rotatable gateway device 4530 may have a generally crescent shape, so that a concave surface 4530(*a*) thereof may receive a circular edge of a puck. The first rotatable gateway device 4530 may receive a puck from the linear track 4588 and may direct it to first circular track 4525. The first rotatable gateway device 4530 may also receive a puck from the first circular track 4525 and may direct it to the linear track 4588. The second rotatable gateway device 4532 may also have a concave surface 4532(*a*) and may operate in a similar manner, allowing pucks to be transitioned from the second circular track 4527 to the linear track 4588, or vice-versa.

The rotatable gateway devices according to embodiments of the invention have a number of advantages. Compared to a gripper, for example, the rotatable gateway devices are less complex and take up less space. Further, the generally crescent shaped rotatable gateway devices can be cooperatively structured with the pucks, so that they temporarily and securely engage the pucks as they are transported from one track to another.

In operation, a primary tube 4522 is identified by the system on the main track 4558 for aliquotting and directed to the aliquotter's aspiration point (A), which may be proximate to the first circular track 4525. The first rotatable gateway device 4530 may receive a puck with a primary tube 4522, rotate, and direct it to the first circular track 4525. Empty pucks 4524 are sent by the system along the main track 4588 behind the puck with the primary tube to the aliquotter's loading point for secondary tubes (B), which may be proximate to the second circular track 4527. An unlimited quantity of empty pucks can be sent for any primary tube. A secondary tube is labeled and loaded into the empty puck 4526 at the aliquotter's loading point for secondary tubes (B) and is directed to the dispensing point (C) proximate to the second circular track 4527. The sample is aspirated from the primary tube at point (A) and dispensed into the secondary tube at point (C). Barcode readers 4523, 4529 at points (A) and (C) verify the correct association. When the aliquotting of the sample into the secondary tube is complete 4528, it is released to its next destination and the next secondary tube moves to the dispensing point (C). The second rotatable gateway device 4532 may receive the puck with the secondary tube with the sample aliquot 4528 from the second circular track 4527 and may transition it to the linear track 4558, by which it leaves the aliquotting unit.

The process can then be completed for any number of additional secondary tubes if the system further routes empty pucks to the aliquotter module. When the last secondary tube is finished, both the last secondary tube and the primary tube are released to their next destinations and the trailing secondary and primary tubes move to the dispensing (C) and aspiration points (A), respectively. The process can then be completed for the trailing secondary and primary tubes.

Figure 5B:
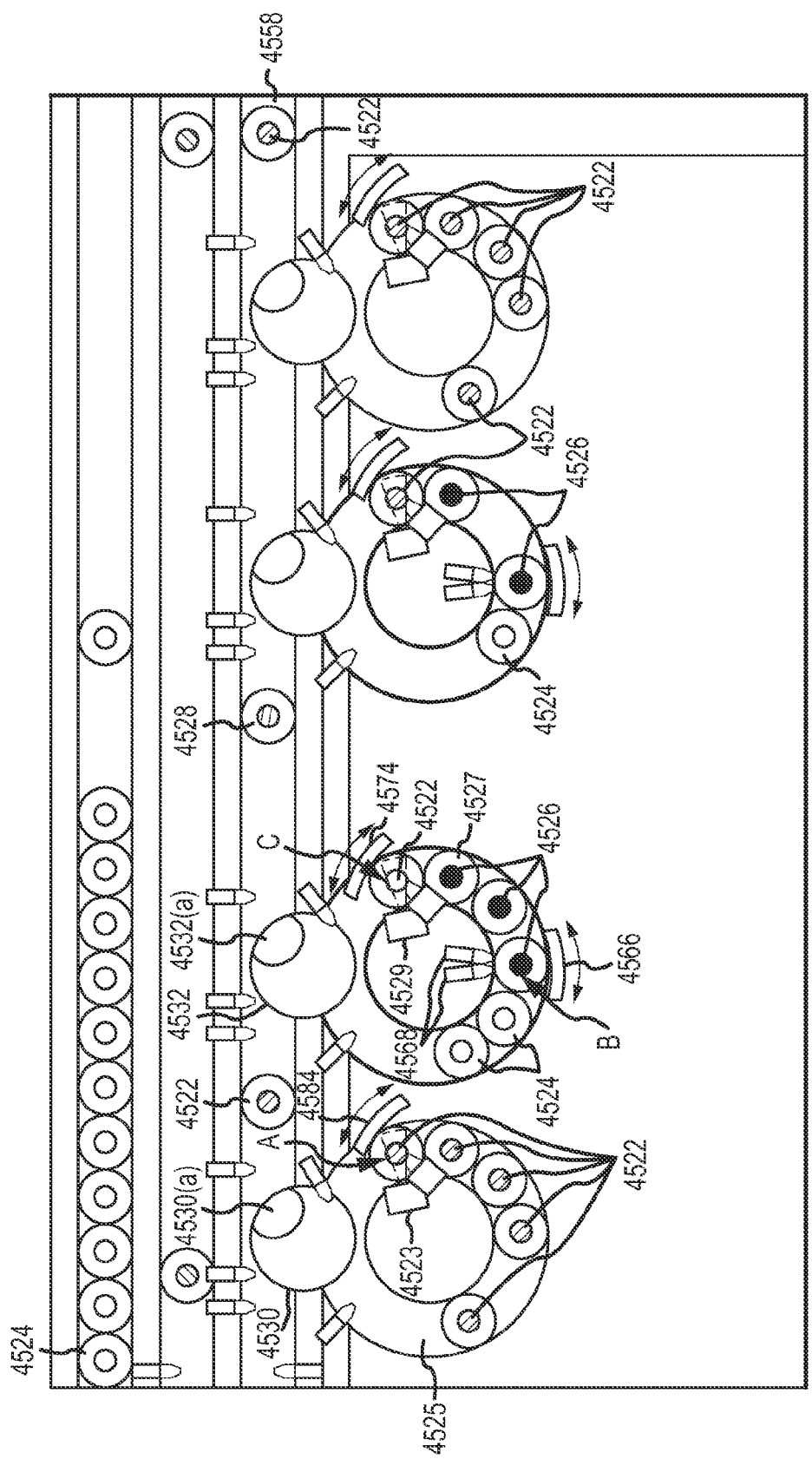
FIG. 5(b) shows a top plan view of a second aliquotter module according to an embodiment of the invention. The second aliquotter module comprises a rotatable gateway device in the form of a disk-like object.
Figure 5C:
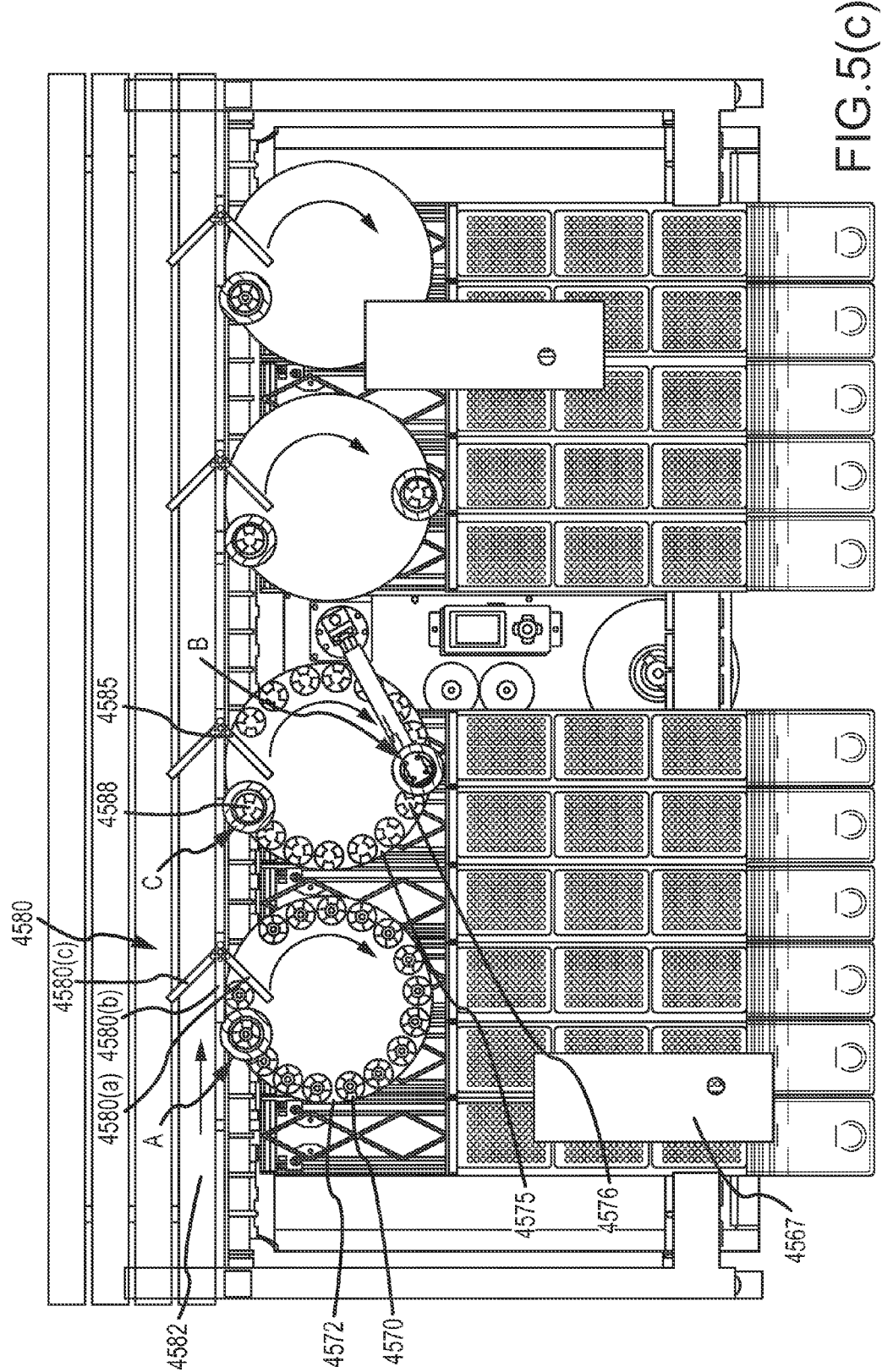
FIG. 5(c) shows a top plan view of a fourth aliquotter module according to an embodiment of the invention. The fourth aliquotter module comprises a rotatable gateway device in the form of a linear bar.

FIG. 5(c) shows another embodiment of the invention. The aliquotter module in FIG. 5(c) comprises linear transport lane 4582, also referred to herein as a travel lane. As in the embodiment in FIG. 5(b), the system comprises first and second circular tracks 4572, 4575.

A number of primary sample containers in pucks 4570 may be on the first circular track 4572, and a number of secondary sample containers in pucks 4576 may be on the second circular track 4575. The pucks may move in a clockwise direction around the tracks.

A first rotatable gateway device 4580 in the form of a bar is adjacent to the first circular track 4572, and can direct pucks between the linear transport lane 4582 and the first circular track 4572. The first rotatable gateway device 4580 may include a first position 4580(a), a second position 4580(b), and a third position 4580(c). The first and third positions 4580(a), 4580(c) may be diverting positions. To move puck 4570 from the first circular track 4572 to the linear transport lane 4582, puck 4570 is hold by a puck manipulator (not shown) while the rotatable gateway device 4580 is moved into its first position 4580(a). The puck 4570 is released from the puck manipulator and moved by the first circular track 4572 to the linear transport lane 4582, by being diverted by rotatable gateway device 4580 in its first position 4580(a). To transfer a puck 4570 from the linear transport lane 4582 to the first circular track 4572, the rotatable gateway device 4580 is moved to its third position 4580(c) before a puck 4570 arrives at the diverting position. As soon as the puck 4570 arrives the diverting position the puck 4570 is diverted by rotatable gateway device 4580 in its third position 4580(c) from the linear transport lane 4582 to the first circular track 4572. A second rotatable gateway device 4585 is positioned adjacent to the second circular track 4575, and can operate in a similar manner to the first rotatable gateway device 4580.

As in the example shown in FIG. 5(b), the system in FIG. 5(c) includes a point (A) where aspiration takes place, a point (B) wherein the loading of secondary sample containers into pucks takes place, and a point (C) where the dispensing of a sample aliquot from the primary sample container to the secondary sample container take place. FIG. 5(c) also shows a pipettor 4567 which can move between the aspiration point (A) and the dispense point (C).

Another embodiment of the invention is directed to a system comprising an aliquotter module comprising a pipettor configured to aspirate a first aliquot volume of a sample in the primary sample container in a first independently movable puck located in an aspiration position and dispense the first aliquot volume of the sample in the secondary sample container in a second independently movable puck located in a dispensing position. The aliquotter module is configured to cause the secondary sample container to leave the aliquotter module before the primary sample container.

FIG. 5(d) shows another aliquotting module according to an embodiment of the invention. There are three linear and parallel lanes 4592, 4594, 4596, formed be two parallel walls, which are part of the aliquotting station. A main transport lane 4590, also referred to herein as a travel lane, is perpendicular to the three lanes 4592, 4594, 4596. An open region 4598 at the end of the three lanes allows pucks to pass between the three lanes 4592, 4594, 4596, and eventually exit the aliquotter module.

In operation, a primary tube 4542 is identified by the system on the main track for aliquotting and is directed to the aliquotter's aspiration point (A), proximate to track 4594. Empty pucks 4544 are sent by the system behind the primary tube to the aliquotter's loading point for secondary tubes (B), proximate to track 4592. An unlimited quantity can be sent for any primary tube. A secondary tube is labeled and loaded into the empty puck 4546 at the aliquotter's loading point for secondary tubes (B) and directed to the dispensing point (C), proximate to track 4592, at the entrance to the open region 4598. The sample is aspirated from the primary tube at (A) and dispensed into the secondary tube at point (C). Barcode readers at points (A) and (C) verify the correct association. When a secondary tube is complete 4548, it is released to its next destination and the next secondary tube moves to the dispensing point (C).

The process can then be completed for any number of additional secondary tubes if the system further routes empty pucks to the aliquotter module. When the last secondary tube is finished, both the last secondary tube and the primary tube are released to their next destinations and the trailing secondary and primary tubes move to the dispensing (C) and aspiration points (A), respectively. The process can then be completed for the trailing secondary and primary tubes.

The pucks that are used in the embodiment in FIG. 5(d) can move independently of each other, and may each contain its own processor, memory, and communication interfaces. In some embodiments, the pucks may communicate with a central control system using a wireless communication mechanism. Further details regarding this type of transport system and other suitable transport systems can be found in U.S. Provisional Patent Application Nos. 61/556,667, 61/616,994, 61/486,126, and PCT Application No. PCT/US2012/037585, which are all herein incorporated by reference in their entirety for all purposes. Further details regarding suitable puck transportation system are also provided below. In some cases, the pucks may be generically referred to as "laboratory product transport elements."

The puck transport system is an autonomous guided vehicle for transporting an individual sample tube. Current chain or belt-driven transportation systems can only control the velocity of the complete track segments. Even if it is possible to have chains with different or even adjustable velocity, it may be difficult to move each individual track with its own velocity. In other words, the puck transport system with the lowest velocity or lowest acceleration/deceleration would dictate the complete segment.

The puck transport system of the present technology provides a transport system that is a self-propelled sample transport unit. The puck transport systems can move samples using the necessary motion parameters and can do so independently from each other. The puck transport systems improve efficiency by maximizing throughput, even with varied statuses for different sample tubes (e.g., normal versus urgent), without the need to sacrifice or risk sample quality of sensitive samples, as each sample can be transported with the maximum velocity. Additionally, the puck transport system may be managed by the central controller or a local intersection controller.

Figure 6:
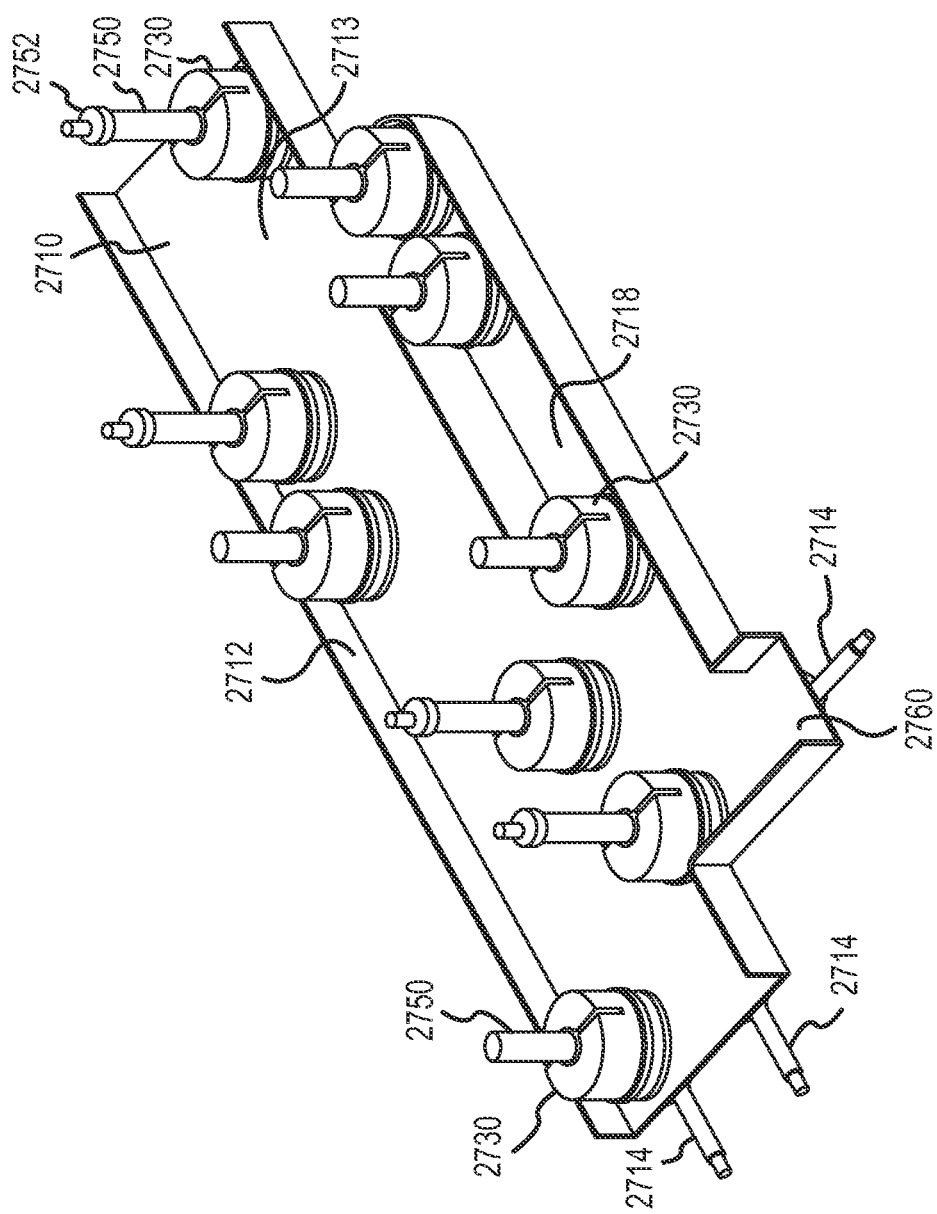
FIG. 6 depicts one example of a perspective partial view of a variant of a transfer path arrangement of a laboratory transport system utilizing the puck transport system.

FIG. 6 shows a perspective partial view of a variant of a transfer path arrangement of a laboratory transport system utilizing the puck transport system. A transfer path 2710, in particular, with side limitation 2712 and a flat horizontal web 2713 are visible. In this example, the side limitation 2712 can be in the form of a raised wall that can at least partially define the transfer path 2710. In this embodiment, there are two raised walls on opposite lateral sides of the flat horizontal web 2713, and the walls and the web 2713 can define the transfer path 2710. Such walls may be of any suitable height depending upon the height of the laboratory product transport element and the sample being carried therein, typically a height of no greater than about 20 mm. Further, the web 2713 can be of any suitable lateral dimensions.

Transfer paths according to embodiments of the technology can also have one or more branches that may lead to other areas. For example, the transfer path 2710 in FIG. 6 can have a lateral branch 2760 that leads to a separation processing station, buffer station, or some other station.

The laboratory transport system can use any suitable numbers or types of devices, which can help guide or move the laboratory product transport elements. As shown in FIG. 6, induction conductors 2714 can be arranged beneath the transfer path 2710. The induction conductors 2714 can be electrically coupled to a high frequency voltage source (not shown), so that they can be supplied with high frequency, in order to generate a high frequency electromagnetic alternating field.

The laboratory product transport elements 2730 that transport sample containers 2750 (e.g., sample tubes) can move on the transfer path 2710. However, the laboratory product transport elements 2730 can be transferred to a processing track 2718 in defined fashion in a row, in order to be able to carry out, for example, optical investigations of the sample material contained in the sample containers 2750.

Electrical conductors 2714 can be provided along the particularly probable paths of the laboratory product transport elements 2730. However, since the laboratory product transport elements 2730 can move independently, they are not bound to the geometry stipulated by the conductors 2714. Their movement is not dependent upon the conductors 2714, as long as the electromagnetic high frequency field generated with conductors 2714 at the location of the laboratory product transport element 2730 is sufficient for corresponding energy transmission or the laboratory product transport element 2730 has energy accumulator 2744 for bridging.

The sample containers 2750 may have any suitable shape or configuration. In some embodiments, the sample containers 2750 may be in the form of tubes. In some cases, covers 2752 may be on the sample containers, while other sample containers do not have a cover on them and are transported open.

Figure 7:
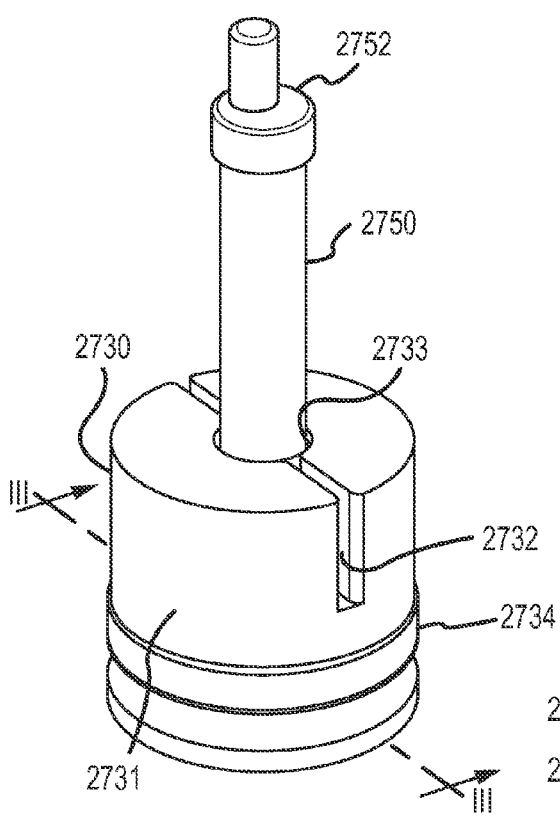
FIG. 7 depicts one example of a perspective view of a laboratory product transport element.

FIG. 7 shows a side perspective view of a laboratory product transport element 2730 according to an embodiment of the technology. The laboratory product transport element 2730 comprises a laboratory product transport element housing 2731, which may have a cylindrical recess 2733 formed at the top of the housing 2731, which may also be cylindrical. A sample container 2750 with a cover 2752 on it may be received in the cylindrical recess 2733. A slit 2732 may be formed in the side of the housing 2731. The slit 2732 can permit optical investigation of the sample material contained in the sample container 2750, and may be coextensive with the recess 2733. In other embodiments, the slit 2732 need not be coextensive with the recess 2733 and may be formed independent of the recess 2733. Furthermore, in other embodiments, the slit 2732 can be an aperture that is in some other form (e.g., a circle).

In this example, the laboratory product transport element 2730 has a round horizontal cross section and has a rubber strip 2734, which serves as an impact protection against the limitations 2712 of the transfer path 2710 or other laboratory product transport elements 2730.

Figure 8:
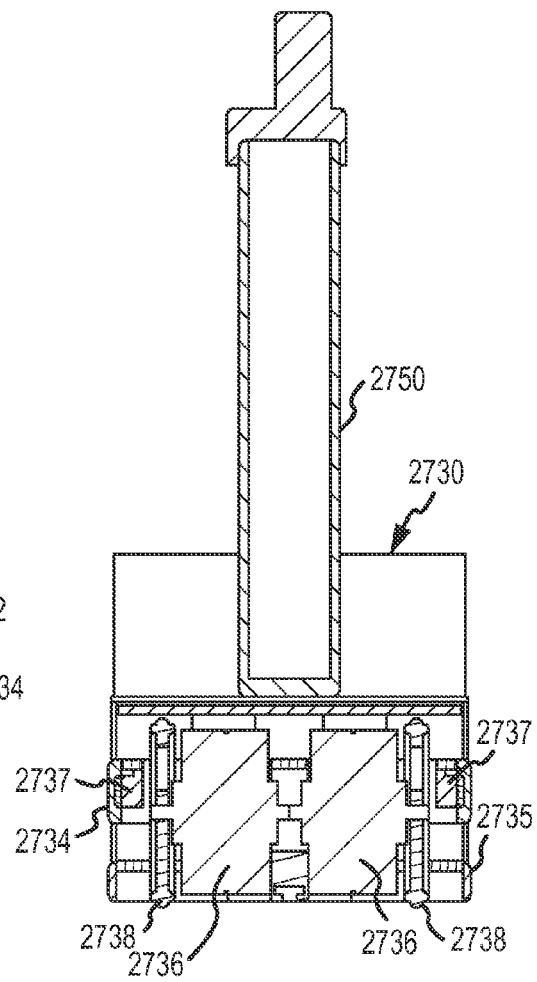
FIG. 8 depicts one example of a side, cross-sectional view of a laboratory product transport element.

FIG. 8 shows a side section of the laboratory product transport element 2730 in the viewing direction III shown in FIG. 7. Reference numbers 2736 denote electric motors that drive rubber wheels or rubber-tired wheels 2738. Two opposite wheels 2738 are provided, which are driven individually by one electric motor 2736 each. The wheels 2730 may be examples of movement devices.

A shoulder 2735 is shown in FIG. 8, which can cooperate, for example, in transfer path channels configure more narrowly with optionally present side protrusions of limitations 2712 of transfer path 2710, in order to hold the laboratory product transport element 2730 down, when the sample container 2750 is to be pulled out upward from recess 2733. The use of shoulder 2735 illustrated in FIG. 8 can be described in further detail in the section "Fine Positioning and Lift-Off." In some embodiments, the laboratory product transport element (not shown in the Figures) can have an anchor-like element. The anchor-like element engages in a corresponding mating piece of the transfer path upon entering a processing station, in order to secure the laboratory product transport element during its stay at the processing station.

The laboratory product transport element 2730 may also comprise distance sensors 2737. In FIG. 8, the distance sensors 2737 may include four distance sensors which are arranged behind the rubber strip 2734 at angles relative to each other. One preferred embodiment is to have all of the sensors facing forward and at an angular relationship to each other of between 10° and 30°, a more preferred embodiment of 20°.

Figure 9:
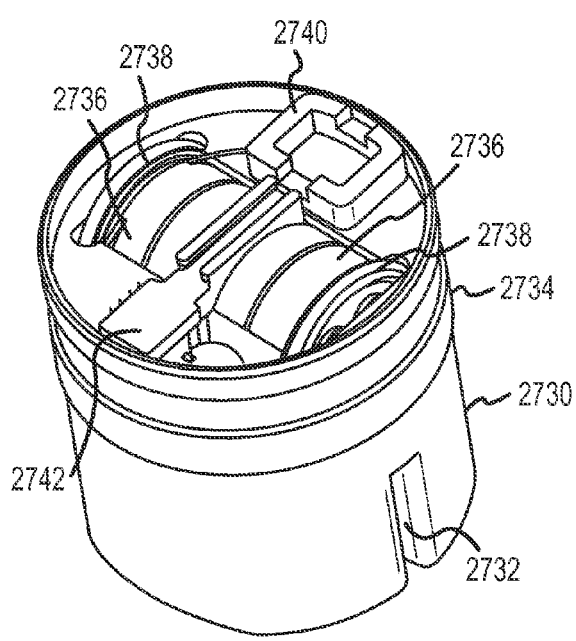
FIG. 9 depicts one example of a bottom perspective view of a laboratory product transport element.

FIG. 9 shows a bottom perspective view of the laboratory product transport element 2730 according to an embodiment of the technology. The induction coil 2740 serves to receive electromagnetic energy from the high frequency fields, which can be generated from electrical conductors 2714 beneath the transfer path.

In some embodiments, it is possible that one or more support wheels are provided, in addition to the driven rubber wheels 2738, so that the laboratory product transport element 2730 rolls on several wheels. However, in other embodiments, no additional wheels are provided, so that the laboratory product transport element, during movement, can lie dragging on one side. This can facilitate curved travel or rotation around its own axis.

In another embodiment of the technology (not shown), the laboratory product transport element 2730 is supported on a ball rotatable in all directions, which is arranged offset to the two driven wheels 2738, in order to avoid dragging on the transfer path. Such a ball can also be used for position detection, as in a computer mouse.

In the embodiment shown in FIG. 9, reference number 2742 denotes a position detector that determines movement of the laboratory product transport element 2730, as in a computer mouse that uses laser light. The traveled surface is then illuminated by an incorporated light source and the reflections taken up with an optical sensor, in order to determine movement of the laboratory product transport element 2730 from them with corresponding image processing algorithms. The position detector 2742 can include a CCD camera and corresponding software, a laser as in a laser mouse, or a ball and sensor as in a ball-type mouse.

Figure 10:
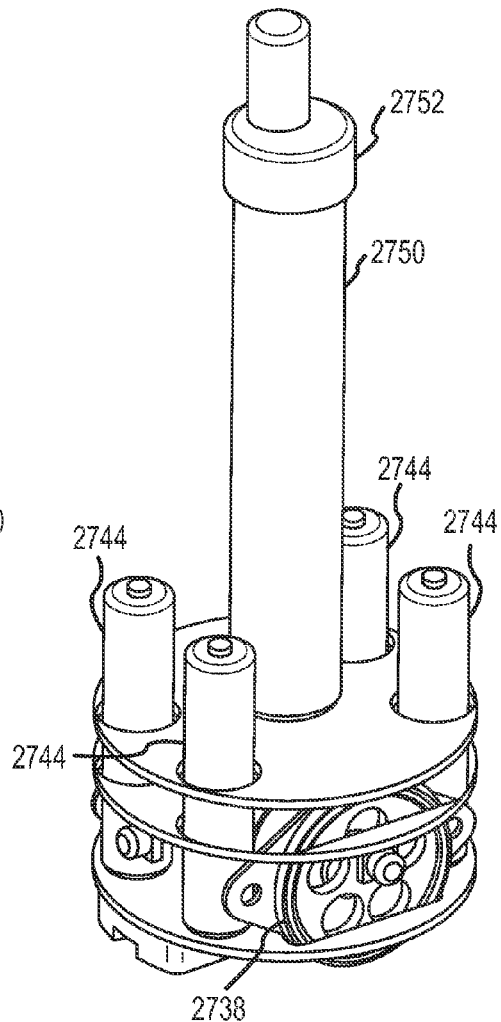
FIG. 10 depicts one example of a laboratory product transport element without external side protection.

FIG. 10 shows the laboratory product transport element 2730 without external side protection. That is, a housing can be removed to show the internal elements of the laboratory product transport element 2730. As shown in FIG. 10, the laboratory product transport element may include batteries 2744. The batteries 2744 can serve to store energy in order to drive of the laboratory product transport element 2730, when the energy generated by the high frequency field of electrical conductors 2714, shown in FIG. 10, and transferred to the induction coil 2740, as seen in FIG. 9, might be too limited. or disabled, to drive the laboratory product transport element 2730. This might be the case, for example, in curves or passing zones.

The laboratory product transport element 2730 also comprises a control unit (not shown), for example, a corresponding microprocessor that receives signals from signal receivers (also not shown). The signal receivers may include infrared light receivers that cooperate with external infrared light transmitters, in order to receive the control signals. Other examples of signal receives may include radio sensors.

Control signals, however, can also be received via the induction coil 2740, as seen in FIG. 9, when corresponding signals are supplied to the electrical conductors 2714, as seen in FIG. 6. Such control signals can be discriminated from the high frequency field that furnishes energy by a corresponding frequency or amplitude modulation.

The laboratory product transport elements 2730 also may optionally have signal transmitters, not shown, in order to produce information and signals. This permits, for example, precise localization of individual selected laboratory product transport elements 2730. The signal transmitters may transmit signals using any suitable frequency and any suitable communications protocol.

Figure 11:
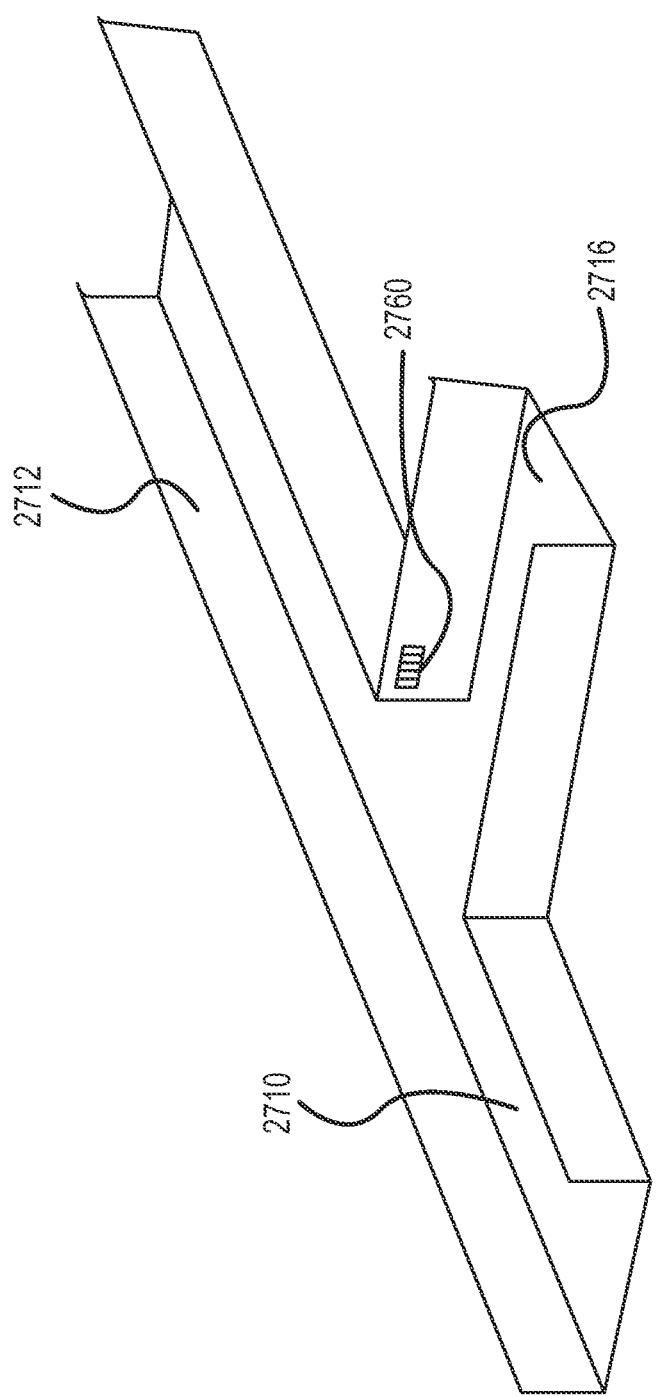
FIG. 11 depicts one example of a cutout of a transfer path.

The laboratory product transport elements 2730 can also have a number of sensors, with which position recognition and fine positioning at processing stations, recognition of the travel path limitation or other laboratory product transport elements, or information exchange is possible. For example, clearly identifiable barcodes can be provided on the transfer path 2710 shown in FIG. 6, either on a side limitation 2712 or a flat horizontal web 2713. The barcodes can be scanned by a laboratory product transport element 2730 with one or more sensors configured as scanners, in order to recognize the precise position of a branch or the precise position of a processing station. An example is shown in FIG. 11 by means of a cutout of a transfer path 2710. A barcode 2760 is situated at a branch 2716, which can be recognized and identified by corresponding scanners of a laboratory product transport element. In this way, the laboratory product transport element obtains information concerning its position. A number of such codes could be provided on the transfer path 2710, which clearly identify the branches, processing tracks, processing stations or the like.

Other possibilities of such orientation features include 2D codes, color marks, reflection films, transponder systems or infrared light transmitters. Suitable sensors capable of sensing such orientation features can be incorporated into the laboratory product transport elements.

The laboratory product transport element 2730 can have a display unit. It can display information as to which path the laboratory product transport element is to take, which laboratory product is being transported, or whether a defect is present. Further, laboratory product transport elements 2730, with signal transmitters and receivers or with display and recording units, can also exchange information with each other either directly via internal communication transmitters, or via a central processor.

In the interior of the laboratory product transport element 2730, a permanent data memory, protected from current failure, can be provided, in which data about the transported laboratory product or data about the path being traveled can be entered.

The diameter of the laboratory product transport element 2730 depicted in the Figures is about 6 cm at a height of about 5.5 cm. The wheels 2738 protrude about 1 mm downward from the laboratory product transport element 2730. The laboratory product transport elements and features thereof may have other suitable dimensions in other embodiments of the technology.

The laboratory product transport element 2730 according to an embodiment of the technology can also have a heating device (not shown). The heating device can keep a sample at a defined temperature during transport or can carry out a defined temperature treatment of the transported sample during the transport. Such a heating device can include, for example, resistance wires which are provided in an appropriate arrangement.

A laboratory transport system according to an embodiment of the technology of the depicted variant can be used, for example, as follows:

Sample containers 2750 are inserted into laboratory product transport elements 2730 at a loading station by using a stationary gripper system or other container transport system. A target is stipulated to the laboratory product transport element via its signal receiver. The geometry of the actual transfer path 2710 can be encoded and entered in a memory of the laboratory product transport element 2730. The control unit of the laboratory product transport element 2730 can identify the stipulated objective by using data about the transfer path geometry entered in the memory and can independently establish an ideal path to this objective. The locations of orientation features, for example, barcode 2760, are also entered in the memory, so that the laboratory product transport element 2730 can orient itself during its travel along a path, and to check its current position or correct it, if necessary.

After a start signal is induced in the laboratory product transport element 2730, the laboratory product transport element 2730 is moved on the pre-defined path established in its memory. If it passes by a barcode 2760, at which a direction change is to be made, the barcode 2760 recorded with the scanner is used as signal by the control unit, in order to make a direction change in the desired direction.

If the laboratory product transport element 2730, for example, reaches a location, at which a direction change is prescribed, one of the drive motors 2736 is stopped or slowed, so that the corresponding wheel 2738 stops or rotates more slowly. In this way, the laboratory product transport element 2730 travels along a curve.

If the laboratory product transport element reaches its destination (e.g., an unloading station) at which a correspondingly programmed laboratory robot is supposed to remove the transported sample container 2750 from the laboratory product transport element 2730, the motors 2736 are stopped. In order to prevent the laboratory product transport element 2730 from being lifted off of the transfer path when the sample container is removed from the recess 2733 of the laboratory transport element, the lateral limitations 2712 of the transfer path 2710 may have inward-facing protrusions that cooperate with the shoulder 2735 on the laboratory product transport element 2730. The lateral inward-facing protrusions can prevent the laboratory product transport element 2730 from being lifted upward if there is friction between the sample container and the recess 2733 of the laboratory product transport element 2730.

In some embodiments, the laboratory product transport element 2730 brings the sample container 2750 to a processing or investigation station, in order to conduct a physical, chemical or biological investigation on the sample. In the case of an optical investigation, the laboratory product transport element 2730 reaches a light source on the side with sample container 2750. A light source can illuminate the lower area of the sample container 2750 through the slit 2732 and emitted light from the sample can be detected by a detector arranged opposite it. The detector or electronics associated with the detector can determine the absorption or fluorescence characteristics of the sample. In order for slit 2732 to lie precisely opposite the correspondingly arranged light source, the laboratory product transport element can be aligned accordingly. This can be achieved by driving the rubber wheels 2738 to rotate in opposite directions. Consequently, the laboratory product transport element 2730 rotates around its own axis, until the slit is arranged opposite the corresponding light source for investigation. The slit can also be used to establish the filling level in the sample container 2750 or to read out a barcode optionally provided in the lower area of the sample tube, which contains information about the transported product.

The laboratory product transport element 2730 can also bring the sample container to one or more processing stations. Suitable processing stations include the stations described above, such as an aliquotting station, a station for closing or opening of the sample containers, stations for conducting optical investigations, and the like. It should be noted that the laboratory transport system may contain active transport systems which interact with the laboratory transport element 2730 by, for example, the movement of a sample container from the laboratory transport element 2730 onto an active transport system (for example, a conveyor belt) using a gripper device, not shown.

Alternatively or additionally, it is also possible to configure laboratory product transport elements so that they can be controlled by external controls. For this purpose, a control unit can be used, and configured to convert control signals in real time to drive signals used by the electric motors 2736. In this way, it is possible to intervene in the automated laboratory process from the outside and to divert or sort out laboratory product transport elements.

It is also possible to fully stipulate the path of the laboratory product transport element 2730, for example, by a wireless program interface. The corresponding program can be entered in the data memory of the laboratory product transport element 2730. The program data can include information as to at which orientation features (e.g., barcode 2760) provided on the limitation 2712 of transfer path 2710, the laboratory product transport element is supposed use to change its direction. In this way, the complete path of the laboratory product transport element 2730, with the corresponding sample containers 2750, is established and programmed into the laboratory product transport element 2730.

If a laboratory product transport element 2730 is defective or becomes inoperable, it can be removed by a user from the transfer path 2710 and can optionally be replaced with a new laboratory product transport element 2730. If this occurs, the disruption to the system is advantageously short and localized. Further, even if intervention is not possible, the system is not blocked. The other laboratory product transport elements 2730 can move around the inoperable laboratory product transport element. The other laboratory product transport elements can be prompted by corresponding control signals from a central processor, or via programming of the individual laboratory product transport elements 2730 to communicate with other such element 2730. For example, the laboratory product transport elements may have corresponding sensors which can detect the presence of a defective or stationary laboratory product transport element 2730 and via programming of the internal control processor move around it.

When they are on the transport path, the individual laboratory product transport elements 2730 can also communicate with each other via optical signal transmitters and receivers. This communication can occur directly and need not be conducted via a centrally provided communication site of the laboratory transport system. In this way, a laboratory product transport element with a particularly sensitive sample can inform other laboratory product transport elements that it has priority.

The energy needed to move the laboratory product transport element 2730 can be obtained from the electromagnetic field via induction coil 2740, which is generated by a high frequency voltage applied to the electrical conductors 2714. The laboratory product transport element 2730 need not precisely follow the electrical conductors 2714. The interaction only needs to be of sufficient duration so that sufficient energy can be picked up from the electromagnetic field in order to drive the drive motors 2736, which drive wheels 2738. When this is not possible, the laboratory product transport element 2730 can have energy accumulators 2744, which supply power to drive motors 2736 at such locations of the transfer path 2710, in which the electromagnetic field of the electrical conductors 2714 is not sufficient. On straight zones, in which the laboratory product transport element 2730 can move close to the electrical conductors 2714, on the other hand, excess energy from the electromagnetic field can be utilized in order to charge the energy accumulators 2744.

Other embodiments of the technology can have photosensitive elements at the bottom of the laboratory product transport element 2730. The photosensitive elements can be illuminated by light bands arranged on the transfer path. The photosensitive elements can be used to furnish electrical drive power.

It is also possible that the laboratory product transport elements 2730 to obtain their drive power completely from energy accumulators 2744. The energy accumulators 2744 can be charged at corresponding charging stations, which can be at processing stations.

VII. Computer Architecture

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 12:
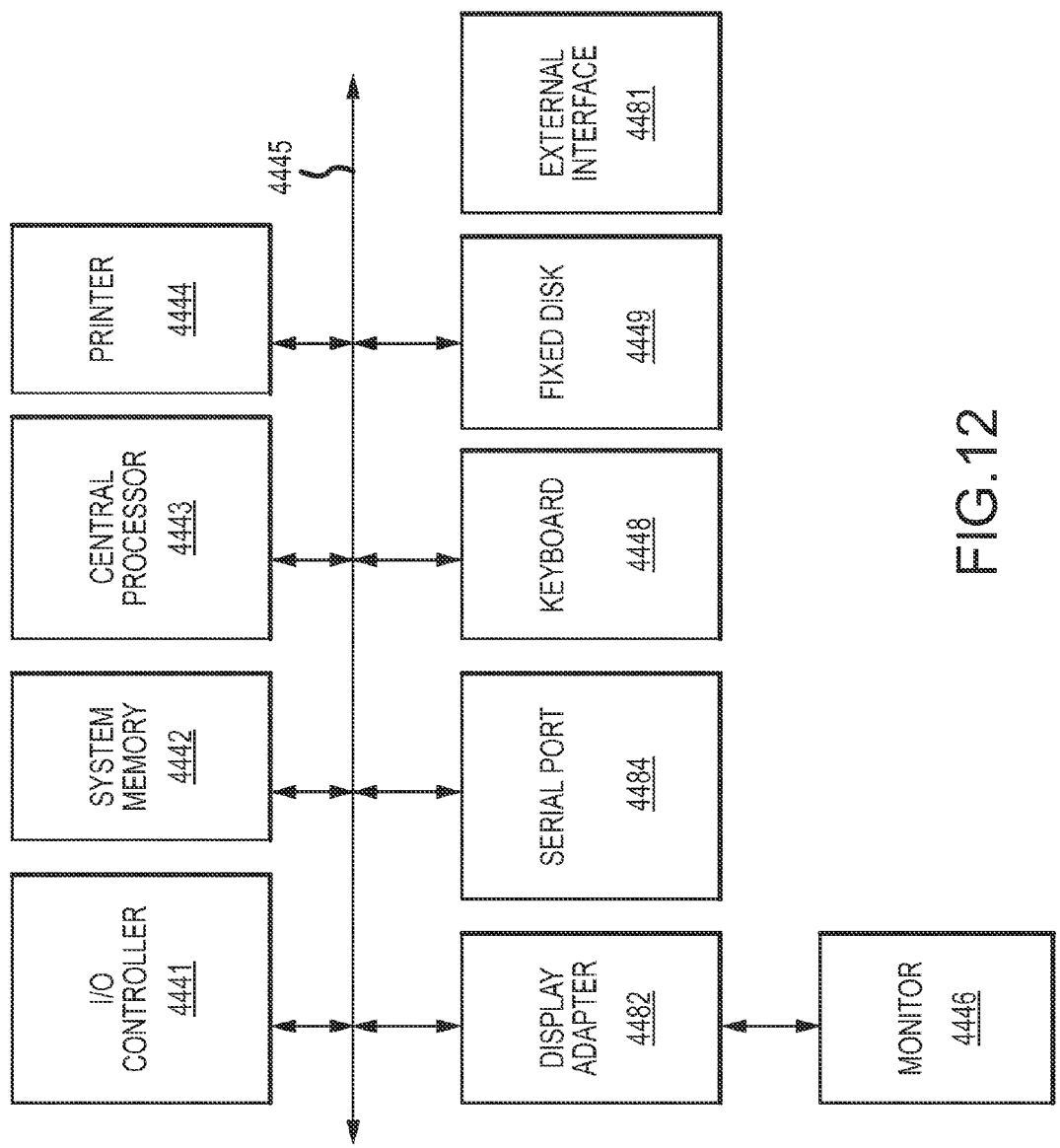
FIG. 12 depicts a block diagram of an exemplary computer apparatus.

Examples of such subsystems or components are shown in FIG. 12. The subsystems shown in FIG. 12 are interconnected via a system bus 4445. Additional subsystems such as a printer 4444, keyboard 4448, fixed disk 4449 (or other memory comprising computer readable media), monitor 4446, which is coupled to display adapter 4442, and others are shown. Peripherals and input/output (I/O) devices, which couple to I/O controller 4441 (which can be a processor or other suitable controller), can be connected to the computer system by any number of means known in the art, such as serial port 4484. For example, serial port 4484 or external interface 4481 can be used to connect the computer apparatus to a wide area network such as the Internet, a mouse input device, or a scanner. The interconnection via system bus allows the central processor 4443 to communicate with each subsystem and to control the execution of instructions from system memory 4442 or the fixed disk 4449, as well as the exchange of information between subsystems. The system memory 4442 and/or the fixed disk 4449 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A system comprising:
an aliquotter module comprising
a track comprising
   a travel lane configured to transport sample carriers with primary sample containers and sample carriers with secondary sample containers,
   a first loop configured to transport empty sample carriers, sample carriers with empty secondary sample containers and sample carriers with secondary sample containers comprising sample aliquots, wherein the first loop is connected to the travel lane such that the sample carriers can enter the first loop from the travel lane and leave the first loop onto the travel lane, and
   a second loop configured to transport sample carriers with primary sample containers, wherein the second loop is connected to the travel lane such that sample carriers can enter the second loop from the travel lane and leave the second loop onto the travel lane, and
a pipettor,
a processor configured to control the pipettor to aspirate a first aliquot volume of a sample in a primary sample container located in an aspiration position and dispense the first aliquot volume of the sample in a secondary sample container located in a dispensing position, wherein the first loop does not include the aspiration position, and wherein the first loop includes the dispensing position, and
the processor further configured to control the aliquotter module to cause the secondary sample container to return to the travel lane before the primary sample container returns to the travel lane.

2. The system of claim 1, wherein the track comprises a common track portion connecting to the first loop and the second loop.

3. The system of claim 1, further comprising:
a first rotatable gateway device proximate the travel lane and the first loop; and
a second rotatable gateway device proximate the travel lane and the second loop,
wherein the first rotatable gateway device is operable to transfer a sample carrier from the travel lane to the first loop and from the first loop to the travel lane, and
wherein the second rotatable gateway device is operable to transfer a sample carrier from the travel lane to the second loop and from the second loop to the travel lane.

4. The system of claim 3, wherein each of the first and second rotatable gateway devices comprise a disk-like object having a crescent shape with a concave surface for receiving a circular edge of a sample carrier.

5. The system of claim 1, wherein the first loop and the second loop are circular endless loops, having no common track portion connecting to the travel lane.

6. The system of claim 1, further comprising sample carriers, wherein the sample carriers are independently movable carriers.

* * * * *